United States Patent [19]

Dorward et al.

[11] Patent Number: 5,403,718
[45] Date of Patent: * Apr. 4, 1995

[54] METHODS AND ANTIBODIES FOR THE IMMUNE CAPTURE AND DETECTION OF BORRELIA BURGDORFERI

[76] Inventors: David W. Dorward, 401 N. 7th St.; Tom G. Schwan, 601 S. 5th St.; Claude F. Garon, 904 Ponderosa Dr., all of Hamilton, Mont. 59840

[*] Notice: The portion of the term of this patent subsequent to Jun. 8, 2010 has been disclaimed.

[21] Appl. No.: 929,172

[22] Filed: Aug. 11, 1992

Related U.S. Application Data

[63] Continuation-in-part of Ser. No. 485,551, Feb. 27, 1990, Pat. No. 5,217,872.

[51] Int. Cl.⁶ .................... G01N 33/569; C07K 15/00
[52] U.S. Cl. .................... 435/7.32; 435/7.94; 530/387.1; 530/388.4; 530/389.5
[58] Field of Search ............ 435/7.32, 7.33, 7.34, 435/7.35, 7.36, 7.37, 243, 261, 962, 7.94; 530/388.4, 389.5, 391.1

[56] References Cited

U.S. PATENT DOCUMENTS 5,008,186 4/1991 Grayston et al. .............. 435/7.36

FOREIGN PATENT DOCUMENTS 8901162 2/1989 WIPO ................ 435/7.35

OTHER PUBLICATIONS

Nowinski et al, Science, 219:637–644 (11 Feb. 1983), "Monoclonal Antibodies for Diagnosis of Infectious Diseases in Humans".

*Primary Examiner*—Carol E. Bidwell

[57] ABSTRACT

The invention relates to novel antigens associated with *Borrelia burgdorferi* which are exported (or shed) in vivo and whose detection is a means of diagnosing Lyme disease. The antigens are extracellular membrane vesicles and other bioproducts including the major extracellular protein. The invention further provides antibodies, monoclonal and/or polyclonal, labeled and/or unlabeled, that react with the antigens. The invention relates to a method for immune capture of specific microorganisms for their subsequent cultivation. The invention is also directed to a method of diagnosing Lyme disease by detecting the antigens in a biological sample taken from a host using the antibodies in conventional immunoassay formats. The invention further relates to kits, for the diagnosis of Lyme disease, comprising the antibodies and ancillary reagents. The advantage of the antibodies used in the invention is that they react with the antigens from geographically diverse strains of *Borrelia burgdorferi*, but do not react with antigens from related Borrelia spirochetes.

2 Claims, 8 Drawing Sheets

METHODS AND ANTIBODIES FOR THE IMMUNE CAPTURE AND DETECTION OF BORRELIA BURGDORFERI

This is a continuation-in-part of copending application U.S. Ser. No. 07/485,551, filed Feb. 27, 1990, now U.S. Pat. No. 5,217,872.

FIELD OF THE INVENTION

The present invention relates to novel antigens associated with *Borrelia burgdorferi*, antibodies that are raised against the antigens and the use of the antibodies to diagnose Lyme disease and for immune capture and cultivation of microorganisms.

BACKGROUND OF THE INVENTION

Since the demonstration of *Borrelia burgdorferi* as the infectious agent of Lyme borreliosis (Burdorfer, W. et at. 1982. Science 216:1317-1319), numerous studies have documented the difficulty of culturing the spirochetes from or observing spirochetes in infected mammalian hosts (Steere, A. C. 1989. New Engl. J. Med. 321: 586-596; Szczepanski, A. et al. 1991. Microbiol. Rev. 55: 21-34). Factors such as the reportedly sparse distribution of *B. burgdorferi* in hosts, the fastidious growth requirements, and the relatively slow growth rate of this spirochete compound the problems associated with aseptic primary isolations.

The immunological interactions between the Lyme disease spirochete, *Borrelia burgdorferi*, and its mammalian hosts are poorly understood (Bosler, E. M., D. P. Cohen, T. L. Schulze, C. Olsen, W. Bernard, and B. Lissman. 1988. Host responses to *Borrelia burgdorferi* in dogs and horses, p. 221-234. In J. L. Benach, and E. M. Bosler (eds.), Lyme disease and related disorders. Annals of the New York Academy of Sciences 539; Dlesk, A., D. F. Bjarnason, P. Mitchell, and P. McCarty. 1988. Lyme disease presenting as seronegative rheumatoid arthritis, p. 454-455. In J. L. Benach, and E. M. Bosler (eds.), Lyme disease and related disorders. Annals of the New York Academy of Sciences 539; Duray, P. H. and A. C. Steere. 1988. Clinical pathologic correlations of Lyme disease by stage, p. 65-79. In J. L. Benach, and E. M. Bosler (eds.), Lyme disease and related disorders. Annals of the New York Academy of Sciences 539; Fox, J. L. 1989. Interest in Lyme disease grows. ASM News 55:65-66; Hyde, F. W., R. C. Johnson, T. J. White, and C. E. Shelburn. 1989. Detection of antigen in urine of mice and humans infected with *Borrelia burgdorferi*, etiologic agent of Lyme disease. J. Clin. Microbiol. 27:58-61; Magnarelli, L. A. 1988. Serologic diagnosis of Lyme disease, p. 154-161. In J. L. Benach, and E. M. Bosler (eds.), Lyme disease and related disorders. Annals of the New York Academy of Sciences 539; Schwan, T. G., W. Burgdorfer, and C. F. Garon. 1988. Changes in infectivity and plasmid profile of the Lyme disease spirochete, *Borrelia burgdorferi*, as a result of in vitro cultivation. Infect. Immun. 56:1831-1836; Schwan, T. G., W. Burgdorfer, M. E. Schrumpf, and R. H. Karstens. 1988. The urinary bladder, a consistent source of *Borrelia burgdorferi* in experimentally infected white-footed mice (*Peromyscus leucopus*). J. Clin. Microbiol. 26:893-895; Sticht-Groh, V., R. Martin, and I. Schmidt-Wolf. 1988. Antibody titer determinations against *Borrelia burgdorferi* in blood donors and in two different groups of patients, p. 497-499. In J. L. Benach, and E. M. Bosler (eds.), Lyme disease and related disorders. Annals of the New York Academy of Sciences 539; Stiernstedt, G., R. Gustafusson, M. Kaarlsson, B. Svenungsson, and B. Skoldenberg. 1988. Clinical manifestations and diagnosis of neuroborreliosis, p. 46-55. In J. L. Benach, and E. M. Bosler (eds.), Lyme disease and related disorders. Annals of the New York Academy of Sciences 539 and Wilske, B., V. Preac-Mursic, G. Schierz, R. Kuhbeck, A. G. Barbour, and M. Kramer. 1988. Antigenic variability of *Borrelia burgdorferi*. p. 126-143. In. J. L. Benach, and E. M. Bosler (eds.), Lyme disease and related disorders. Annals of the New York Academy of Sciences 539). Most mammalian hosts mount an antibody response to the spirochete, however the antibodies are often serologically cross-reactive with other species of Borrelia, and individuals with sero-negative infections have been encountered using standard screening criteria (Dlesk, A., D. F. Bjarnason, P. Mitchell, and P. McCarty. 1988. Lyme disease presenting as seronegative rheumatoid arthritis, p. 454-455. In J. L. Benach, and E. M. Bosler (eds.), Lyme disease and related disorders. Annals of the New York Academy of Sciences 539; Fox, J. L. 1989. Interest in Lyme disease grows. ASM News 55:65-66; Hyde, F. W., R. C. Johnson, T. J. White, and C. E. Shelburn. 1989. Detection of antigen in urine of mice and humans infected with *Borrelia burgdorferi*, etiologic agent of Lyme disease. J. Clin. Microbiol. 27:58-61; Magnarelli, L. A. 1988. Serologic diagnosis of Lyme disease, p. 154-161. In J. L. Benach, and E. M. Bosler (eds.), Lyme disease and related disorders. Annals of the New York Academy of Sciences 539; Sticht-Groh, V. R. Martin, and I. Schmidt-Wolf. 1988. Antibody titer determinations against *Borrelia burgdorferi* in blood donors and in two different groups of patients, p. 497-499. In J. L. Benach, and E. M. Bosler (eds.), Lyme disease and related disorders. Annals of the New York Academy of Sciences 539 and Wilske, B., V. Preac-Mursic, G. Schierz, R. Kuhbeck, A. G. Barbour, and M. Kramer. 1988. Antigenic variability of *Borrelia burgdorferi*. p. 126-143. In. J. L. Benach, and E. M. Bosler (eds.), Lyme disease and related disorders. Annals of the New York Academy of Sciences 539:126-143). Furthermore, strain variation among *B. burgdorferi* isolates, and antigenic variation within populations render immunodiagnostics, based on monoclonal antibodies, potentially insensitive and unreliable for detection of circulating and excreted antigens in some hosts (Barbour, A. G., R. H. Heiland, and T. R. Howe. 1985. Heterogeneity of major proteins in Lyme disease borreliae: a molecular analysis of North American and European isolates. J. Infect. Dis. 152:478-484 and Wilske, B., V. Preac-Mursic, G. Schierz, R. Kuhbeck, A. G. Barbour, and M. Kramer. 1988. Antigenic variability of *Borrelia burgdorferi*. p. 126-143. In. J. L. Benach, and E. M. Bosler (eds.), Lyme disease and related disorders. Annals of the New York Academy of Sciences 539:126-143). Therefore, clinical symptoms, patient history and occasional primary isolations of the spirochete from blood or tissue biopsies, provide the bases for most diagnoses (Benach, J. L., E. M. Bosler, J. P. Hanrahan, J. L. Coleman, G. S. Habicht, T. F. Bast, D. J. Cameron, J. L. Ziegler, A. G. Barbour, W. Burgdorfer, R. Edelman, and R. A. Kaslow. 1983. Spirochetes isolated from the blood of two patients with Lyme disease. N. Engl. J.

Med. 308:740–742; Dlesk, A., D. F. Bjarnason, P. Mitchell, and P. McCarty. 1988. Lyme disease presenting as seronegative rheumatoid arthritis, p. 454–455. In J. L. Benach, and E. M. Bosler (eds.), Lyme disease and related disorders. Annals of the New York Academy of Sciences 539:454–455; Duray, P. H., and A. C. Steere. 1988. Clinical pathologic correlations of Lyme disease by stage, p. 65–79. In J. L. Benach, and E. M. Bosler (eds., Lyme disease and related disorders. Annals of the New York Academy of Sciences 539:65–79 and Rawlings, J. A., P. V. Fornier, and G. J. Teltow. 1987. Isolation of Borrelia spirochetes from patients in Texas. J. Clin. Microbiol. 52:1148–1150.20). Such problems are often cited as factors influencing the reportedly poor diagnostic acumen for Lyme disease (Fox, J. L. 1989. Interest in Lyme disease grows. ASM News 55:65–66).

Considerable work is currently directed toward identifying conserved, species-specific cell surface antigens for diagnostic use, and for epidemiological and pathogenetic studies. Expression of outer surface protein A (OspA) is considered universal among B. burgdorferi isolates, but not among related spirochetes (Barbour, A. G., R. H. Heiland, and T. R. Rowe. 1985. Heterogeneity of major proteins in Lyme disease borreliae: a molecular analysis of North American and European isolates. J. Infect. Dis. 152:478–484; Barbour, A. G., S. L. Tessier, and W. J. Todd. 1983. Lyme disease spirochetes and ixodid tick spirochetes share a common surface antigenic determinant defined by a monoclonal antibody. Infect. Immun. 41:795–804; Bergstrom, S., V. G. Bundoc, and A. G. Barbour. 1989. Molecular analysis of linear plasmid-encoded major surface proteins, OspA and OspB, of the Lyme disease spirochaete Borrelia burgdorferi. Mol. Microbiol. 3:479–486; Hyde, F. W., R. C. Johnson, T. J. White, and C. E. Shelburn. 1989. Detection of antigen in urine of mice and humans infected with Borrelia burgdorferi, etiologic agent of Lyme disease. J. Clin. Microbiol. 27:58–61; Magnarelli, L. A. 1988. Serologic diagnosis of Lyme disease, p. 154–161. In J. L. Benach, and E. M. Bosler (eds.), Lyme disease and related disorders. Annals of the New York Academy of Sciences 539:154–161 and Wilsek, B., V. Preac-Mursic, G. Schierz, R. Kuhbeck, A. G. Barbour, and M. Kramer. 1988. Antigenic variability of Borrelia burgdorferi, etiologic agent of Lyme disease. J. Clin. Microbiol. 27:58–61 and Wilske, B., V. Preac-Mursic, G. Schierz, R. Kuhbeck, A. G. Barbour, and M. Kramer. 1988. Antigenic variability of Borrelia burgdorferi p. 126–143. In J. L. Benach, and E. M. Bosler (eds.), Lyme disease and related disorders. Annals of the New York Academy of Sciences 539:126–143). This protein is immunogenic, however, surface-exposed regions appear to be antigenically variable, since surface-reactive monoclonal antibodies to OspA fail to recognize some isolates (Barbour, A. G., R. H. Heiland, and T. R. Howe. 1985. Heterogeneity of major proteins in Lyme disease borreliae: a molecular analysis of North American and European isolates. J. Infect. Dis. 152:478–484; Hyde, F. W., R. C. Johnson, T. J. White, and C. E. Shelburn. 1989. Detection of antigen in urine of mice and humans infected with Borrelia burgdorferi. p. 126–143. In. J. L. Benach, and E. M. Bosler (eds.), Lyme disease and related disorders. Annals of the New York Academy of Sciences 539:126–143).

Recent experiments have shown that OspA and several other proteins are exported from B. burgdorferi cells in membrane vesicles (Garon, C. F., D. W. Dorward, and M. D. Corwin. 1989. Structural features of Borrelia burgdorferi— Lyme disease spirochete: silver staining for nucleic acids. Scanning Microscopy Supplement 3, pages 109–115; Dorward, D. W., T. G. Schwan, and C. F. Garon, 1991. J. Clin. Microbiol. 29:1162–1171). Indirect evidence suggests these vesicles may be produced by spirochetes in vivo providing sustained antigenic challenge to hosts maintaining a limited population of spirochetes (Fox, J. L. 1989. Interest in Lyme disease grows. ASM News 55:65–66). To determine whether B. burgdorferi vesicles occur in experimentally-infected mice, polyclonal rabbit sera were generated against vesicles and an 83 kilodalton (kDa), major extracellular protein (MEP). Using these reagents, a 2-stage immune electron-microscopic assay was developed for first capturing then identifying extracellular B. burgdorferi infections.

The closest known technology to the present invention was a diagnostic kit, initially produced by 3M Corp. (Fast Lyme, Cat. No. 700–500) that used monoclonal antibodies to detect Lyme antigen in human urine samples. The kit was limited to urine samples, provided false-negative results with geographically diverse samples, and was marginally sensitive (Hyde F. W. et al, (1989), Detection of antigen in urine of mice and humans infected with Borrelia burgdorferi, etiologic agent of Lyme disease, J. Clin. Microbiol. 27:58–61). Moreover, the kit technology, owned by BioWhittaker, is neither FDA approved for human testing nor currently marketed.

SUMMARY OF THE INVENTION

The present invention relates to a method for isolation and concentration of specific microorganisms from a biological source. The method allows for the specific immune capture and subsequent cultivation of the isolated microorganism.

The invention relates to novel antigens associated with Borrelia burgdorferi which are exported (or shed) in vivo and whose detection is a means of diagnosing Lyme disease. The antigens are extracellular membrane vesicles and other bioproducts including the major extracellular protein. Another object of the invention is to provide antibodies, monoclonal and/or polyclonal, labeled and/or unlabeled, that are raised against the antigens. A further object of the invention is to provide a method of diagnosing Lyme disease by detecting the antigens in a biological sample taken from a host using the antibodies in conventional immunoassay formats. Another object of the invention is to provide kits, for the diagnosis of Lyme disease, comprising the antibodies and ancillary reagents. The advantage of the antibodies used in the invention is that they react with the antigens form geographically diverse strains of Borrelia burgdorferi, but do not react with antigens from related Borrelia spirochetes.

DETAILED DESCRIPTION OF THE INVENTION

Figure 1:
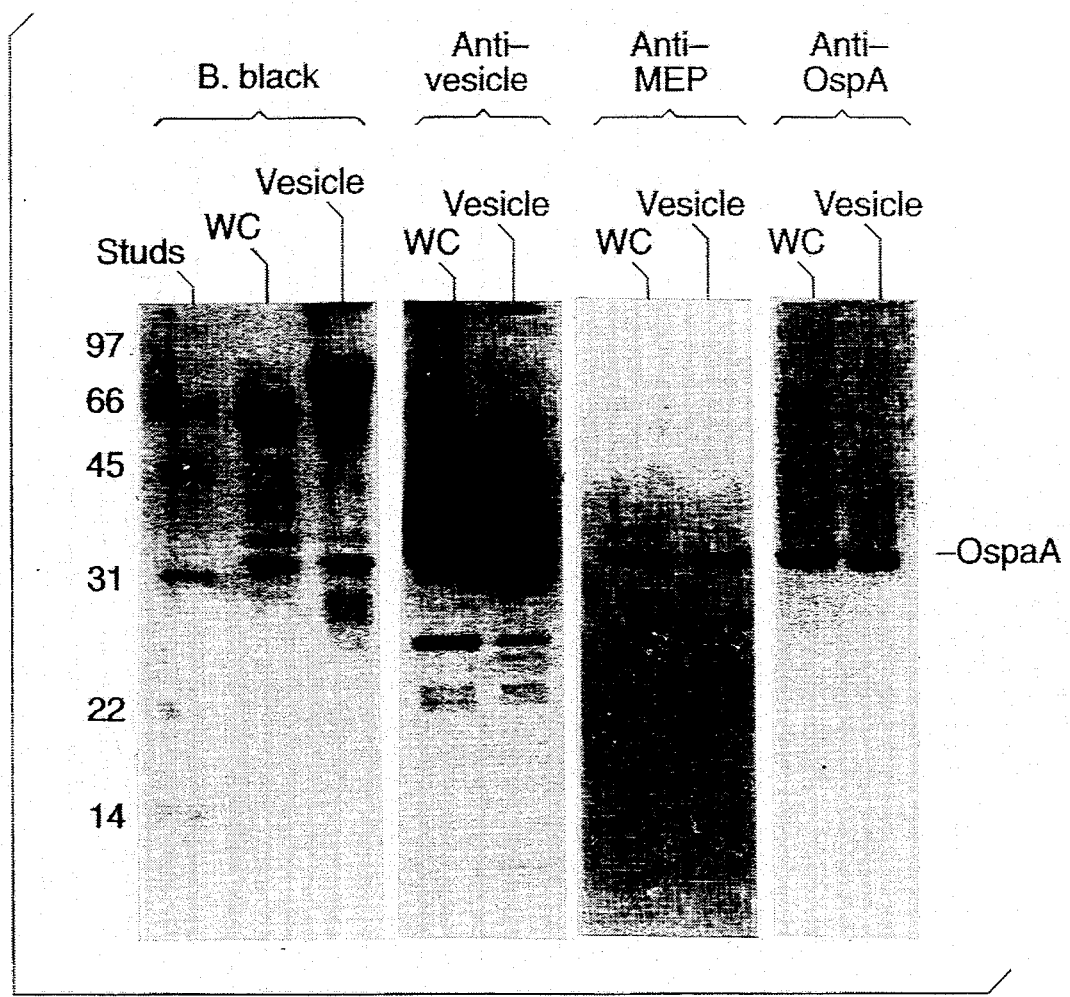
FIG. 1. Immunoblot analysis of antibodies used for the capture and detection of B. burgdorferi antigens.
Figure 2A:
FIG. 2. a–c Localization of epitopes recognized by IgG directed against the major extracellular protein (MEP).
Figure 2B:
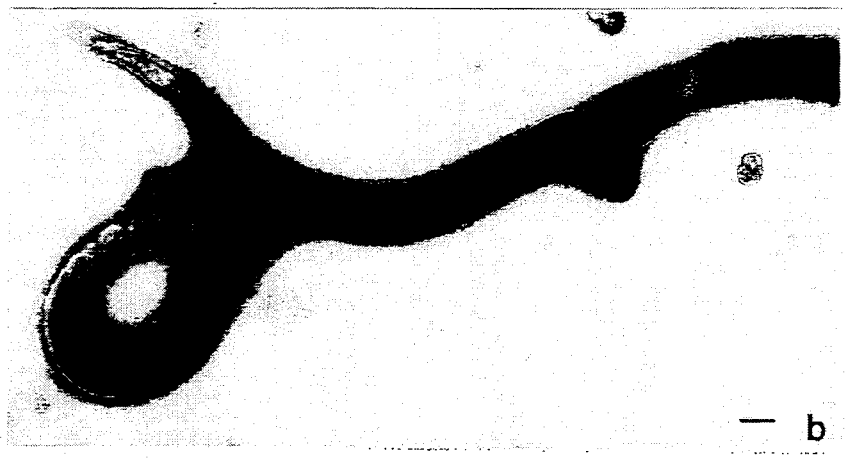
Figure 2C:
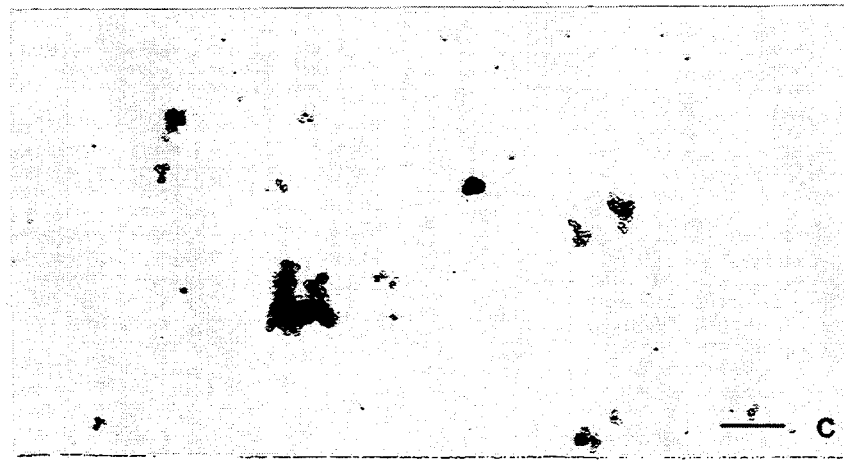
Figure 3A:
FIG. 3. a–f Immune electron microscopic detection of B. burgdorferi antigens in mammalian urine and blood.
Figure 3B:
Figure 3C:
Figure 3D:
Figure 3E:
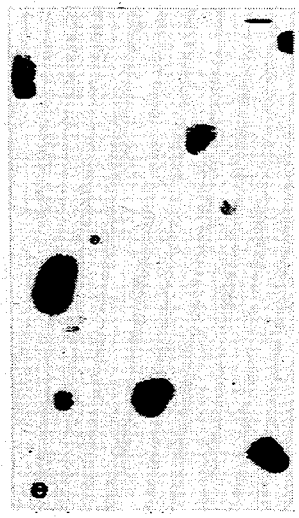
Figure 3F:
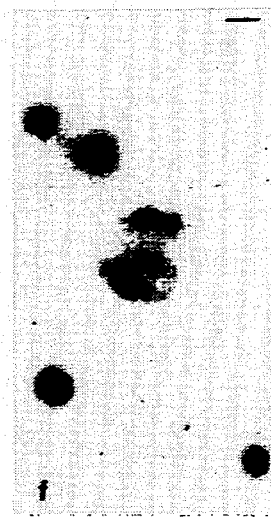
Figure 4A:
FIG. 4. a–h Detection of B. burgdorferi antigens in macerated ixodid ticks and mouse tissues.
Figure 4B:
Figure 4C:
Figure 4D:
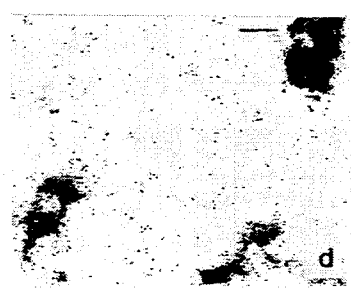
Figure 4E:
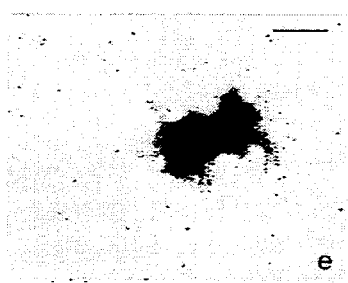
Figure 4F:
Figure 4G:
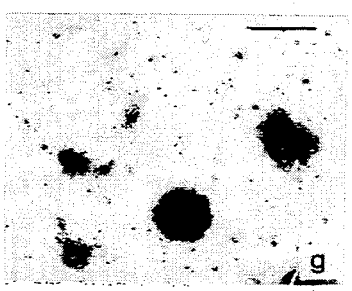
Figure 4H:
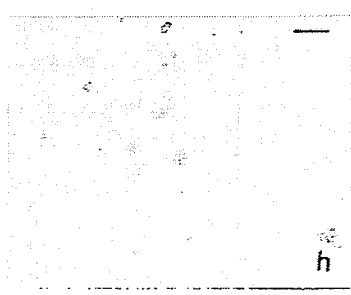

The present invention is useful in capturing microorganisms from a source material onto surfaces coated with antibodies directed against certain surface components of a microorganism. The microorganisms that are isolated by the present invention include bacteria, fungi and parasites. The microorganisms include nonpathogenic, pathogenic and potentially pathogenic microorganisms. The captured microorganism is placed into sterile medium for aseptic cultivation. The present invention of immune capture and cultivation is useful in isolating a specific microorganism that is difficult to obtain as a pure culture from a source containing a mixture of different microorganisms especially if the organism of interest is in low numbers as compared to the other microorganisms in the mixture.

The sources include but are not limited to environmental sources such as soil, water, air. The present invention allows microorganisms from water supplies, waste treatment sites, oil spills, mines, and agricultural areas to be isolated by immune capture and cultivated.

Also of interest as a source are tissues and fluids from ticks, lice, reduviid bugs, mosquitoes, flies, and other vectors known or suspected of being involved in the transmission of infectious microorganisms to animals.

Of particular interest as a source are tissues and fluids from a host such as an animal, preferably mammal, containing or suspected to contain the microorganism of interest. The present invention is especially useful in isolating or immune capturing microorganisms that occur at low density in tissues and fluids of infected hosts or which may also contain potential contaminants. The present invention is particularly useful in isolating pathogenic or potentially pathogenic microorganisms including but not limited to bacteria, fungi and parasites.

Potentially pathogenic microorganisms that are immune captured and cultivated using the present invention include, but are not limited to, intestinal and/or food-borne pathogens such as:

*Escherichia coli, Shigella dysenterae, Shigella flexneri, Salmonella typhi, Salmonella typhimurium, Yersinia enterocolitica, Campylobacter jejuni, Helicobacter pylori, Clostridium perfringens, Clostridium botulinum, Staphylococcus aureus, Bacteroides fragilis,* and the like.

Oral pathogens or potentially pathogenic microorganisms that are isolated from the oral cavity of a host using the immune capture and cultivation technique of the present invention include, but are not limited to, *Bacteroides gingivitis, Streptococcus mutants, Streptococcus sanguis, Treponema denticola,* and the like.

Respiratory and/or air-borne pathogens or potential pathogens that are isolated using the present invention from samples such as bronchial secretions, oral-nasal passages, pleural fluid and lung biopsy samples include, but are not limited to, *Streptococcus pneumonia, Streptococcus pyogenes, Bordetella pertussis, Haemophilus influenzae, Pseudomonas aeruginosa, Mycobacterium tuberculosum, Mycobacterium avium, Mycoplasma pneumonia, Legionella pneumophila, Listeria monocytogenes, Neisseria meningitidis, Chlamydia psittaci,* and the like.

Sexually-transmitted pathogens, or potential pathogens that are isolated and cultivated from samples taken from the oral, rectal, genital, ocular regions of a host and secretions from these regions using the immune capture and cultivation method of the present invention, include, but are not limited to *Neisseria gonorrhoeae, Chlamydia trachomatis, Treponema pallidum, Trichomonas vaginalis* and the like.

Vector-borne pathogens or potential pathogens are isolated and cultivated from infected host tissues or host fluids and from infected tissues or fluids from vectors such as ticks, mites, lice using the present invention of immune capture and cultivation. Examples of such vector-borne pathogens or potential pathogens include but are not limited to *Yersinia pestis, Rickettsia rickettsii, Rickettsia akari, Rickettsia prowazekii, Rickettsia tsutsugamushi, Coxiella burnetti, Borrella burgdorferi, Borrelia hermsii, Borrelia duttoni,* and the like.

Disseminated pathogens or potential pathogens that are isolated from infected host tissues or host fluids using immune capture and cultivation include, but are not limited to, *Leptospira interrogans, Bacillus anthracis, Francisella tulerensis* and the like.

Protozoan and/or parasite pathogens or potential pathogens are also isolated and cultivated using the present invention. Such protozoans and parasites include, but are not limited to, *Toxoplasma gondii*, Plasmodium species, Trypanosoma species, *Pneumocystis carinii*, Schistosoma species, Leishmania species, and the like.

The organisms are isolated from infected host tissue and host fluids as well as from tissue and fluid samples taken from the vectors. Vectors for the protozoans and parasites are generally known in the art and include, but are not limited to, mosquitoes, flies, reduviid bugs and the like.

The present invention of immune capture and cultivation is also useful in isolating pathogenic or potentially pathogenic fungi from the tissues or fluids of an infected host. An example of such a yeast includes *Candida albicans* and the like.

The immune capture method is particularly useful in capturing and cultivating pathogenic microorganisms with fastidious growth requirements and/or require anaerobiosis and microorganisms that have relatively slow growth rates. Examples of microorganisms with relatively fastidious growth requirements, include but are not limited to, *Campylobacter jejuni, Helicobacter pylori, Treponema denticola, Mycobacterium tuberculosum, Mycobacterium avium, Mycoplasma pneumonia, Legionella pneumophila, Listeria monocytogenes, Neisseria meningitidis, Chlamydia psittaci, Neisseria gonorrhoeae, Chlamydia trachomatis, Treponema pallidum, Rickettsia rickettsii, Rickettsia akari, Rickettsia prowazekii, Rickettsia tsutsugamushi, Coxiella burnetti, Borrelia burgdorferi, Borrelia hermsii, Borrelia duttoni, Borrelia turicatae, Leptospira interrogans, Francisella tulerensis,* and the like.

Examples of microorganism with anaerobic growth requirements include, but are not limited to, *Clostridium perfringens, Clostridium botulinum, Bacteroides fragilis, Bacteroides gingivalis, Bacillis anthracis,* and the like.

Of particular interest is the spirochete, *B. burgdorferi*, which occurs at an apparently low density in tissues and fluids of infected hosts. This microorganism can be captured using the present invention, and retained on surfaces containing adsorbed antibodies directed toward cell-surface extracellular *B. burgdorferi* antigens. Relatively few contaminating, non-*B. burgdorferi* organisms or host cells adhere to antibody-activated surfaces so that pure or relatively pure cultures of *B. burgdorferi* are obtained upon culturing of the captured microorganisms.

Microorganisms are captured onto antibody-activated surfaces, and cultivated by transferring such surfaces into culture medium. The culture media and conditions for culturing the above identified microorganism, as well as other microorganisms, are known in the art and are detailed in Bergey's Manual of Systemic Bacteriology (Eds. John G. Holt et al., Williams & Wilkins, Baltimore-London, Vol. I-1984, Vol. II-1986, Vol. III & IV-1989), incorporated herein by reference. The immune capture system facilitates aseptic primary isolation of microorganisms from biological and/or environmental samples such as infected tissues soil, water, air, and the like.

Antibodies useful in the immune capture method for isolating specific microorganisms are antibodies that react with external components of the microorganisms. Such external components include but are not limited to cell surfaces, surface coats, cell walls, slime layers, extracellular flagella, pili and the like. The antibodies are produced by immunizing mammals with the intact microorganism or with purified or partially purified external components of the microorganism. The antibodies are also produced by immunizing mammals with modified external components of the microorganism or using synthetic peptides, carbohydrates, lipopolysaccharides, glycoproteins, glycolipids or recombinant peptides or proteins, the structures of which one deduces from the naturally occurring microorganism. These antibodies are capable of binding and retaining intact microorganisms onto antibody-activated surfaces for isolation and subsequent cultivation. Preferred antibodies are antibodies that are species-specific and thus are capable of binding to a particular species of microorganism. The antibodies are polyclonal, or monoclonal, and may be a cocktail of antibodies with different reactivities for the microorganism of interest.

Mammalian lymphocytes are immunized in vivo or in vitro for production of antibodies. For in vivo immunizations of mammals, immunizations are repeated as necessary at intervals of up to a few weeks (e.g., 2–4 weeks) so as to obtain a sufficient titer of antibodies. The microorganism, external component of the microorganism, or the like is injected into the animal in appropriate solutions or adjuvants via an appropriate route (i.e., intramuscular, intraperitoneal, subcutaneous, intravenous, intradermal, and the like).

If monoclonal antibodies are desired, the hybridoma formation and monoclonal antibody production may be carried out using many different techniques which are well known in the art. (Campbell, A. M. 1984. Monoclonal Antibody Technology. Laboratory Techniques in Biochemistry and Molecular Biology (ed. R. H. Burdon and P. H. van Knippenberg), Vol. 13. Elsevier, Amsterdam; Goding, J. W. 1986. Monoclonal Antibodies: Principles and Practice, 2nd edition, Academic Press, London; Kipps, T. J. et al. 1986, In: Handbook of Experimental Immunology: Applications of Immunological Methods in Biomedical Sciences, 4th ed. (ed. D. M. Weir et al.), Vol 4, p. 108, Blackwell Scientific Publications, Oxford; Harlow, E. et al. 1988, Antibodies: A Laboratory Manual, Cold Spring Harbor Laboratory, Cold Spring Harbor, N.Y., all incorporated herein by reference). Basically, spleen cells from a hyperimmunized animal are fused with cells from a genetically marked myeloma that has been adapted to grow in tissue culture. Mixed populations of the resulting hybrid cells are tested for their ability to secrete antibody of the desired specificity, and clones derived from individual cells are then established. The resulting monoclonal antibodies are screened for their ability to specifically immune capture the target microorganism of interest while not binding to non-target microorganisms.

The antibodies or antigen binding fragments of the antibodies may also be produced by genetic engineering. The technology for expression of both heavy and light chains of antibody molecules in *E. coli* is the subject of the PCT patent applications, publication numbers WO 901443, WO 901443, and WO 9014424 and in Huse et al., 1989 Science 246: 1275–1281, incorporated herein by reference.

An antibody-activated, capillary tube-based selective culture system was designed that allows the selective immobilization of *B. burgdorferi* cells and cultivation of the spirochete. In this system, IgG antibodies, specific for *B. burgdorferi*, generated against extracellular membrane vesicle concentrates, or against an extracellular 83 kDa multi-protein complex, are adsorbed onto the inner surface of capillary tubes. Suspensions of spirochetes containing or lacking contaminating bacteria, or specimens from infected hosts are drawn within the tube, and incubated. After expelling the contents of the tubes, the tubes are washed with sterile buffer and placed in culture medium containing or lacking antibiotics. *B. burgdorferi* can be selectively and aseptically cultured in vitro from pure and mixed cultures and in vivo from tissue or fluid samples using this system.

The surface to which the antibodies are bound may be glass, plastics, and the like. When a glass surface is used it may be pretreated with a basic solution such as 1N NaOH or other agent, to permit complete wetting of the surface, before the antibody containing solution is added. Such pretreatment allows for an even layer of antibody solution to coat the surface.

Surfaces activated with antibodies dissolved in phosphate-buffered saline are used to capture spirochetes and successfully inoculate fresh growth medium. The tubes are used immediately after coating with the antibody solution, or stored wet, to avoid extensive salt deposits, from the phosphate-buffered saline, that occur with drying. Tubes coated with antibody dissolved in phosphate-buffered saline were efficient in retention of *B. burgdorferi*, and exclusion of contaminating *E. coli*.

When long term storage of antibody coated tubes is needed, the tubes are coated with antibody in a solution of ammonium bicarbonate. Ammonium bicarbonate, a volatile buffer, is removed under vacuum, leaving an antibody film on the surface of the glass. Antibody activated tubes produced using ammonium bicarbonate allowed recovery of *B. burgdorferi* from a mixture of *B. burgdorferi* and *E. coli*, and provided long term storage capabilities.

The immune capture method of isolating microorganisms is capable of isolating specific microorganisms from biological samples containing a variety of different microorganisms with or without the use of supplemental antibiotics. For example, antibody-activated capillary tubes were capable of isolating *B. burgdorferi* from mixed cultures, containing *S. aureus* along with *E. coli*, without the use of supplemental rifampin. Overnight growth of the serial dilutions of the mixed cultures suggested nearly a 10-fold excess of contaminating bacteria in the original mixture. Using the present invention of immune capture, *B. burgdorferi* was successfully recovered from samples. Thus, both in systems supplemented with or lacking rifampin, the capillary tubes coated with antibodies enabled purification of *B. burgdorferi* from mixed cultures at nearly the same rate as from a diluted pure culture of *B. burgdorferi*. Using control tubes that were not coated with antibodies, recovery rates from pure cultures of *B. burgdorferi* were reduced by 100–1000 fold, and *B. burgdorferi* could not be recovered from mixed cultures.

Using tubes coated with the anti-83 (kilodalton) kda antibodies, *B. burgdorferi* spirochetes were recovered from infected tick and murine samples. No isolates of *B. burgdorferi* were obtained by direct inoculations of media with preparations from the infected tick and murine samples.

Variables may be modified to increase the probability for successful isolation of this organism, or to target other organisms for cultivation. The present immune capture system may be modified for use with other substrates such as polystyrene, with enhanced antibody-binding affinities, to increase the capacity for capturing organisms. Similarly, repeated contact of comparatively large volumes of source material to antibody activated surfaces may allow for retention of additional targeted microorganisms, providing an increased chance of effective isolation. Furthermore, since rinsing apparently reduces the level of contaminants from immobilized spirochetes, such immune capture methods facilitate amplification of *B. burgdorferi* DNA target sequences by polymerase chain reaction. The present immune capture system is capable of detecting and obtaining isolates of pathogenic or free-living microorganisms for diagnostic genetic, pathogenic, therapeutic, or other experimental purposes.

Current biological and serological techniques for diagnosing *Borrelia burgdorferi* infections are often inconclusive. In order to monitor Lyme disease, a rapid and sensitive assay was developed for *B. burgdorferi* antigens infected hosts. Polyclonal rabbit antisera were raised against membrane vesicles, and against an 83 kDa vesicle protein, purified from in vitro *B. burgdorferi* cultures. Immunoglobulin G (IgG) was recovered from these sera and tested for species-specific reaction with several geographically diverse Borrelia isolates. Parlodion-coated electron microscope grids were activated with anti-vesicle $F(ab')_2$ fragments, then incubated with fluids or macerated tissues from ticks, mice, dogs, and humans. Captured antigens were assayed by immune electron microscopy using anti-83 kDa antibodies (that is, antibodies raised against the 83 kDa MEP) and protein A-colloidal gold conjugates. The results showed that Lyme spirochetes shed surface antigens which were readily detectable in urine, blood, and several organs from infected hosts. Positive mouse urine titers exceeded $1\times10^6$. Intact spirochetes were frequently observed on grids incubated with blood, spleen, or bladder preparations, and *B. burgdorferi* was re-isolated from all experimentally-infected mice. Immunoblot analysis confirmed the presence of extracellular antigens in positive mouse and human urine samples. These results reconfirm that *B. burgdorferi* antigens persist in a variety of host materials. Such antigens can be captured and identified with specific polyclonal antibodies, providing a sensitive assay for diagnosing and studying lyme borreliosis.

Accordingly, the present invention relates to a sensitive immunoassay and diagnostic test kit for the detection of *B. burgdorferi*-specific antigens in ticks, mice, dogs, and humans. When the assay involves the immune capture of antigens with immobilized $F(ab')_2$ fragments, it is followed by specific antigen detection using polyclonal IgG. A reagent capable of reacting with polyclonal IgG (e.g., labeled protein A, labeled protein G, or labeled antipolyclonal IgG antibodies) may be used during the assay. Using this assay, *B. burgdorferi* antigens and occasionally intact spirochetes were detected in ticks and mammalian urine, blood, and organs.

In one embodiment, a reagent capable of binding to immunoglobulin molecules is used in the detection method. The reagent or immunoglobulin binding factor may bind specifically to a immunoglobulin class such as IgG on IgM or may bind to any immunoglobulin class. Examples of such immunoglobulin binding factors include but are not limited to protein A and protein G, and the like.

When the detection method involves the use of protein A or protein G, the capture antibodies must be, F(ab')2 or F(ab) fragments generated against extracellular membrane vesicle concentrates. Protein A binds to intact IgG. Either intact antibodies or the antigert binding fragments can be used. When protein A, protein G, or other reagent which binds to the Fc portion of antibodies is used, the capture antibody must be a fragment.

Antigens were captured with $F(ab')_2$ fragments. Initial characterizations of the anti-vesicle sera by immunoblot analysis and immune electron microscopy demonstrated that serum IgG recognized multiple cell and vesicle surface components including OspA and OspB, however, the sera also recognized some other host antigens. Anti-vesicle $F(ab')_2$ effectively concentrated and immobilized antigens from complex mixtures, and appeared to block nonspecific adsorption of host material and assay reagents to coated electron microscopic grids. Because these antibodies cross-reacted with some host antigens, a second antibody was used for specific detection of *B. burgdorferi* antigens.

The detection antibody was generated against the 83 kDa MEP. Surprisingly, immunoblots showed that the resulting polyclonal sera recognized OspA at 31 kDa and OspB at 34 kDa, but had relatively weak activity with the original immunogen. Concurrent studies have shown that OspA and the MEP appear to be glycosylated with a variety of carbohydrates (Dorward, D. W., and C. F. Garon, 1990. Use of antibody and lectin-colloidal gold conjugates to detect surface and extracellular glycoproteins produced in vivo by the Lyme disease spirochete *Borrelia burgdorferi* in: Peachey, L. D., and D. B. Williams (eds.) Electron Microscopy, 1990, Proceedings of the XIIth International Congress for Electron Microscopy, Vol. 3: Biological Sciences. San Francisco Press, Inc., San Francisco, Calif. pp. 934–935). Whether glycosylation or possible protein homology accounts for these results remains unclear. The finding that the anti-MEP IgG recognizes *B. burgdorferi* antigens at 83 kDa in mouse urine, and 11, 14, 22, 31, and 34 kDa in human urine, suggests that either common epitopes are expressed in several exported proteins, or the MEP readily dissociates into subunits or degradative products.

As with previous characterizations of anti-OspA monoclonal antibodies (Barbour, A. G., R. H. Heiland, and T. R. Howe. 1985. Heterogeneity of major proteins in Lyme disease borrelia: a molecular analysis of North American and European isolates. J. Infect. Dis. 152:478–484; Hyde, F. W., R. C. Johnson, T. J. White, and C. E. Shelburn. 1989. Detection of antigen in urine of mice and humans infected with *Borrelia burgdorferi*, etiologic agent of Lyme disease. J. Clin. Microbiol. 27:58–61 and Wilske, B., V. Preac-Mursic, G. Schierz, R. Kuhbeck, A. G. Barbour, and M. Kramer. 1988. Antigenic variability of *Borrelia burgdorferi*. p. 126–143. In. J. L. Benach, and E. M. Bosler (eds.), Lyme disease and related disorders. Annals of the New York Academy of Sciences 539:126–143), the anti-MEP polyclonal IgG was species-specific. Furthermore, whereas anti-OspA monoclonal antibodies invariably fail to bind some strains, this polyclonal antibody recognized all strains of *B. burgdorferi* tested, including several geographically diverse isolates. We presume that the polyclonal IgG binds to multiple epitopes on OspA and MEP. Hence, divergence among *B. burgdorferi* strains, reflected by amino acid sequence variation within these proteins, could occur without complete loss of antibody recognition.

When these reagents were used to examine experimentally-infected mice by electron microscopy, *B. burgdorferi*-derived material was detected in urine, blood, and macerated urinary bladder, spleen, liver, and brain tissues. Aggregated antigens were not observed in kidney tissue, however the relatively dense deposition of gold in kidney preparations suggests *B. burgdorferi* antigens were present. Minimal background labeling on control grids lacking antigen and on grids incubated with material from uninfected mice and humans, indicated that gold deposition in this assay was specific for *B. burgdorferi* antigens.

Intact spirochetes were observed on grids incubated with mouse blood, and with bladder and spleen tissue specimens from mice. A spirochete was also observed in 1 μl of a human urine sample, suggesting this detection system may facilitate studies of tissue involvement complicated by difficulty in demonstrating spirochetes in infected hosts (Fox, J. L. 1989. Interest in Lyme disease grows. ASM News 55:65–66).

Pre-incubation of the grids with anti-vesicle F(ab')2 fragments dramatically increased the sensitivity of antigen detection, particularly in complex samples such as blood and macerated tissues. Flocculent antigen was detectable in these samples without pre-incubations, however the grids contained considerable quantities of unlabeled host material. Apparently, the F(ab')2 fragments functioned both by concentrating Borrelia antigens on the grids, and blocking non-specific adsorption of eukaryotic material.

Vesicles were resolved on the surfaces of spirochetes adhering to grids incubated with infected tissues, indicating these vesicles are produced by *B. burgdorferi* in vivo. Gold-labeled, membranous vesicles were also observed in urine and blood. The majority of specific gold labeling occurred on flocculent material detected in *B. burgdorferi* cultures and all infected animals. While structurally-similar material was frequently on cell surfaces, its exact nature is currently unknown. Western blots showed that anti-MEP IgG and anti-OspA monoclonal antibodies react with the same bands. Further experimentation showed that continued immunization of rabbits with the 83 kDa band resulted in the production of IgG antibodies which also recognized OspB (Dorward, Schwan, & Garon, 1991. J. Clin. Microbiol. 29:1162–1171). Previous work showed that *B. burgdorferi* sloughs OspA from cell surfaces (Barbour, A. G., S. L. Tessier, and W. J. Todd 1983. Lyme disease spirochetes and ixodid tick spirochetes share a common surface antigenic determinant defined by a monoclonal antibody. Infect. Immun. 41:795–804). Together these results suggest that the MEP, OspA and possibly OspB share identity and may be components of a surface or s-layer that can be released from cell surfaces.

The detection of antigens in urine using monoclonal antibodies has recently been reported (Hyde, F. W., R. C. Johnson, T. J. White, and C. E. Shelburn. 1989. Detection of antigen in urine of mice and humans infected with *Borrelia burgdorferi*, etiologic agent of Lyme disease. J. Clin. Microbiol. 27:58–61). The following Example 1 confirms that finding, and provides methods that may enhance the reported sensitivity of detection (Hyde, F. W., R. C. Johnson, T. J. White, and C. E. Shelburn. 1989. Detection of antigen in urine of mice and humans infected with *Borrelia burgdorferi*, etiologic agent of Lyme disease. J. Clin. Microbiol. 27:58–61). Example 1 also shows that extracellular *B. burgdorferi* antigens occur in tissues in which spirochetes are infrequently reported (Duray, P. H., and A. D. Steere. 1988. Clinical pathologic correlations of Lyme disease by stage, p. 65–79. In J. L. Benach, and E. M. Bosler (eds.), Lyme disease and related disorders. Annals of the New York Academy of Sciences 539:65–79). Such results suggest either that large quantities of circulating antigert are deposited in these tissues, or that the antigen is secreted by a limited number of migrating spirochetes and the antigen persists in situ. The possible pathological effects of this material are unknown, however determining its nature and the mechanisms behind its deposition my lead to better a understanding of *B. burgdorferi* pathobiology. The reagents developed in Example 1 as discussed herein below should facilitate such determinations.

Both the F(ab')2 and IgG preparations proved stable when stored as lyophilized powder. In these experiments the reagents were rehydrated just prior to use, indicating appropriate preparations could be stored and distributed in aliquots for use as needed. Combining immune capture with polyclonal antigen detection should reduce false-negative detection of *B. burgdorferi*, resulting from minor antigenic variation, and enable reliable demonstrations of this spirochete and its products in vector, reservoir host, domestic animal, and human urine, blood, or tissue samples. Although designed initially for careful electron microscopic examination of captured antigens, the system is readily adaptable to more common clinical laboratory analysis protocols.

These clinical laboratory analysis protocols are well known in the art. The antibodies, particularly those raised against the MEP, can be used in all the conventional immunoassay formats to detect the antigens in biological samples, and thus detect the presence of *Borrelia burgdorferi*. Both homogeneous and heterogeneous immunoassays may be used. The anti-MEP antibody can be directly labeled with conventional labels, i.e., enzymes, radioisotopes, fluorophores, colloidal metals (gold), or these labels can be attached to antibody binding proteins (anti-anti-MEP antibodies, protein A, etc.)

to indirectly label the anti-MEP antibody. A preferred method of detecting the exported antigens is as follows. The anti-vesicle antibodies are bound to an inert solid substrate. The biological sample is brought into contact with this substrate under conditions conducive for the formation of immune complexes between the anti-vesicle antibodies and any antigens associated with *Borrelia burgdorferi* antigens in the sample. These antigens include the intact *Borrelia burgdorferi* spirochete, the extracellular membrane vesicles, and the exported proteins from the surface of the spirochete, including the 83 kDa MEP, and the 11, 14, 22, 31 and 34 kDa exported proteins found in human urine as described in Example 1. The substrate is washed and then brought into contact with anti-MEP antibodies under condition conducive to form a ternary sandwich immune complex consisting of an anti-vesicle (antigen) anti-MEP complex. The anti-MEP antibody can be directly labeled (see above) in which case the sandwich immune complex is directly detected. Alternatively, the substrate with its ternary sandwich immune complex can be washed and then the anti-MEP antibody portion of the complex is detected by means well known in the art. For example, a labeled anti-anti-MEP antibody can be used; if the anti-MEP antibody was raised in species A (a rabbit for example), then a labeled anti-A antibody raised in a different species (i.e., mouse anti-rabbit) could be used to detect the anti-MEP in the ternary complex. Other labeled specific binding proteins that bind to the anti-MEP antibody can be used, such as protein A. The most preferred method of detecting the exported antigens uses F(ab')$_2$ fragments made from the anti-vesicle antibodies bound to an inert solid substrate, an unlabeled anti-MEP IgG antibody and labeled protein A for detection. The results of Example 1 support the discussions and conclusions referred to hereinabove.

The present invention has proven effective for use with tears, urine, blood, and tissue biopsies from mammals, and with crushed ticks. The use of pooled polyclonal, instead of monoclonal, antibodies reduces the potential for loss of recognition caused by genetic and antigenic variation among *B. burgdorferi* isolates. Furthermore, the sensitivity of this system for antigen detection in titered urine is at least 10$^4$ times greater than reported by the 3M study. This conclusion is based upon the findings of the present inventors when urine is diluted 1:2 million and upon the report of a dilution of 1:64 (Hyde, F. W. et al (1989), Detection of antigen in urine of mice and humans infected with *Borrelia burgdorferi*; etiologic agent of Lyme disease, J. Clin. Microbiol. 27:58–61).

Accordingly, the present invention relates to a method for detecting the presence of specified microorganisms in samples, which comprises capturing *Borrelia burgdorferi* antigens in said sample with F(ab')$_2$ fragments, F(ab) fragments or with intact or untreated antibody molecules (e.g., IgG or IgM) raised against the extracellular membrane vesicles exported from *Borrelia burgdorferi*; and contacting the captured antigens with polyclonal antibodies raised against the 83 kDa MEP. The capture and contact of the antigens and antibodies may occur in physiological saline such as Dulbecco's phosphate-buffered saline (dPBS). In addition, the *Borrelia burgdorferi* antigens in said sample may be captured with immobilized F(ab')$_2$ fragments, immobilized F(ab) fragments or immobilized intact antibody molecules capable of binding *Borrelia burgdorferi* antigens. The polyclonal antibodies may be radioactively labeled and the resulting antigen/IgG complex may readily be detected by radioimmunoassay (Gee, A. P. and J. J. Langone (1983), Immunoassay using antigen-coated plastic tube on radiolabeled or enzyme labeled protein A, Methods Enzymol. 92:403–413; Umetsu, D. T., R. S. Geha (1987), In vitro production of antibody in cultures of human peripheral blood lymphocytes. Methods Enzymol. 150:309–316). Alternatively, the polyclonal antibodies may be contacted with a reagent (e.g., labeled) capable of reacting with polyclonal antibodies and the antibody/reagent complex is then detected. For instance, the antibody/reagent complex may be visually detected through a microscope. Preferably, the polyclonal antibodies are of IgG class and a reagent capable of reacting with polyclonal IgG is a protein A conjugate, such as manufactured by Sigma Chemical Company, St. Louis, Mo. (e.g., protein A gold, Catalog No. P1039). Other suitable reagents capable of reacting with IgG include commercially available protein G conjugates or similar anti-IgG antibody conjugates. Protein G gold conjugates are available from Sigma Chemical Co., St. Louis, Mo., Catalog No. P1671.

Although the polyclonal antibodies of the invention are preferred, a system containing various monoclonal antibodies functioning as a polyclonal system is also within the scope of the present invention.

The use of the term "F(ab')$_2$ fragments" when describing reagents for the specific capture of *Borrelia burgdorferi* antigens encompasses the use of "F(ab) fragments" or intact antibodies for this purpose.

Various samples can be tested for the presence of bioproducts indicative of the presence of Lyme disease spirochete in unknown biological samples by the method of the present invention. For diagnosis of Lyme disease a body sample from a patient suspected of being infected will normally be diluted in an appropriate solution such as physiological saline and this solution will then be contacted with the diagnostic device containing the substrate and the immobilized F(ab')$_2$ fragments. Then, the antigen is detected with polyclonal IgG raised against the 83 kDa MEP and a reagent capable of reacting with polyclonal IgG such as a protein A conjugate. When testing for the presence of bioproducts indicative of the presence of the Lyme disease spirochete in, for instance, the blood of a patient to be tested, the blood is drawn from the patient in a routine manner and the blood is then optionally placed in a sterile solution. This solution will then be tested for the presence of bacteria. The biological sample may comprise mammalian urine, blood, tears, cerebral spinal fluid, synovial fluid and the like or organs. The organ may be selected from the group consisting of but not limited to macerated urinary bladder, spleen, liver, lung, heart, kidney and brain tissue. The sample may also comprise an ixodid tick.

Various insoluble substrates to which the F(ab')$_2$ fragments can be bound may be used. The substrate should be capable of easily binding the F(ab')$_2$ fragments without interfering with the diagnostic test to be conducted. Possible substrates include glass; thin layer chromatographic materials such as silica gel; synthetic plastic material such as polyvinyl chloride, polystyrene, polypropylene and polyethylene. The substrates may be in the form of flat plates, glass beads, thin layers on another substrate, microtiter plates, Petri dishes, latex beads, agarose or other types of beads, filter paper, nylon filter membranes, bacterial or other types of cells, glass slides, glass tubes, plastic tubes, etc. The substrate may also be in the form of a membrane or film of either a porous or nonporous nature. Preferably, the F(ab')$_2$ fragments may be immobilized to an insoluble substrate such as a solid surface selected from the group consisting of Parlodion-coated electron microscopy grids, nitrocellulose filter membranes, glass cover slips and microtiter wells and the like.

The F(ab')$_2$ fragments should be bound to the substrate in an amount sufficient to and in a manner which allows binding of the antigens to be detected to the F(ab')$_2$ fragments. From a practical point of view, the F(ab')$_2$ fragments will usually be present in an amount of at least 0.1 ng/mm$^2$, more preferably at least 1-1.7 ng/mm$^2$ of surface area of the substrate. As far as the upper limit of the concentration of the F(ab)2 fragments on the substrate, the F(ab')$_2$ fragments can be bound to the saturation density of the substrate. For instance, the saturation density of F(ab')$_2$ fragments on polystyrene is established in a routine manner for a given manufacturers substrate (Engvall, E. and P. Perlmann (1972), Enzyme-linked immunosorbent assay, ELISA III, Quantification of specific antibodies by enzyme-labeled anti-immunoglobulin in antigen coated tubes, J. Immunol. 109:129-135; Voller A., D. Bidwell, G. Huldt, and E. Engvall (1974), A microplate method of enzyme-linked immunosorbent assay and its application to malaria, Bull. Wld. Hlth. Org. 51:209-211). The F(ab')$_2$ fragments can be bound as a molecular monolayer which substantially completely covers the surface area of the substrate. Use of more than a molecular monolayer F(ab')$_2$ fragments bound to the substrate may result in a waste of materials and may result in inefficient binding of the F(ab')$_2$ fragments to the substrate. Preferably, the substrate is saturated with the F(ab')$_2$ fragments after experimentally determining the optimal quantity of F(ab')$_2$ fragments to use with a given substrate.

The F(ab')$_2$ fragments may be bound to the substrate in any suitable manner. Covalent or non-covalent (e.g., hydrophobic) bonding may be used to bind the F(ab')$_2$ fragment to a substrate. Other forms of bonding such as ionic bonding may be used. Intact antibody molecules or F(ab) fragments may be substituted for F(ab')$_2$ fragments provided the substituted reagents can retain *Borrelia burgdorferi* antigens on the substrate, without causing non-specific cross-reaction with the detection reagents described herein.

The F(ab')$_2$ fragments may also be bound to particles, such as latex particles, which are thereafter immobilized by embedding in or binding to a porous membrane. The latex particles may be of a size which can be embedded by pressure into the pores of the porous membrane. Thus, for example, the average particle size of the latex particles may be about the same as, or slightly smaller than, the average surface pore size of said porous membrane. Alternatively, the particles may be bound to any porous or liquid permeable material such as a screen, net, etc. A material such as a binder may be used to bind the particles to the support as long as the binder does not interfere with the ability of the F(ab')$_2$ fragments to bind microorganisms.

The samples suspected of containing *Borrelia burgdorferi* or its exported antigens is contacted with the substrate containing the F(ab')$_2$ fragments described hereinabove. Preferably, the solution is contacted with the substrate until or before equilibrium is reached, e.g., 10 to 120 minutes, more preferably 30 to 60 minutes at a temperature of 20° to 37° C., preferably 25° to 37° C. The precise time and temperature conditions are selected to provide sufficient time for the bacterial antigens to adsorb the F(ab')$_2$ fragments to a degree sufficient to allow for accurate testing. The sample to be tested may be dissolved and/or diluted with various liquids such as physiological saline, etc.

After the solution has been contacted with the substrate containing the F(ab')$_2$ fragments for a time sufficient to allow the bacterial or antigens exported by the bacteria to bind to the F(ab')$_2$ fragments, the substrate is optionally washed to remove all unbound materials.

A test is then conducted to determine the presence of the bacteria or antigens exported by the bacteria bound to the F(ab')$_2$ fragments on the substrate. Various tests to accomplish this purpose are known in the art such as the enzyme linked immunosorbent assay (ELISA), a radioimmune assay test, direct or indirect fluorescent antibody test, etc. Basically, the substrate containing the F(ab')$_2$ fragments and suspected of containing bacterial antigen bound thereto is contacted with a material which binds to the bacterial antigen to be tested. Such materials include, for example, antibodies against the bacterial antigen (e.g., polyclonal IgG). The substrate/F(ab')$_2$ fragment/antigen/polyclonal IgG complex is labeled with a reagent capable of reacting with polyclonal IgG such as protein A conjugates, protein G conjugates, etc.

Reagents such as protein A and protein G may be "labeled" with a substance which may be easily detected. For example, the protein A may be conjugated with an enzyme, radioactive material or element or fluorescent material. If the protein A is conjugated with an enzyme, the substrate is thereafter contacted with a substrate for the enzyme which preferably turns color upon contact with the enzyme thereby indicating a positive reaction. The protein A to be used should be one which reacts with the polyclonal IgG but which does not react with the F(ab')$_2$ fragments bound to the substrate thereby preventing a false positive reading. If the protein A is radioactively labeled, then the presence of radioactivity on the substrate should be measured. It is also possible that the protein A may be fluorescently labeled. In this situation the treated substrate should be exposed to ultraviolet light to determine the presence of the fluorescent labeled material bound to the substrate. Preferably, the protein A conjugates may be selected from the group consisting of colloidal gold, fluorescent materials such as fluorescein isothiocyanate, rhodamine, latex beads or other suitable beads, biotin, avidin, enzymes such as horseradish peroxidase and alkaline phosphatase. Other suitable reagents capable of reacting with polyclonal IgG include protein G conjugates, similar anti-IgG antibody conjugates and direct conjugates with anti-MEP IgG, or F(ab) or F(ab')$_2$ fragments made from anti-MEP IgG.

The detection system of the invention has proven effective at detecting antigert in mouse urine diluted 1:2,000,000 in dPBS (physiological saline).

The present invention is further directed to a diagnostic kit for detecting the presence of *Borrelia burgdorferi* or exported antigens, comprising F(ab')$_2$ fragments, F(ab) fragments or intact or untreated antibody molecules, capable of capturing and retaining *Borrelia burgdorferi* antigens; polyclonal antibodies raised against the 83 kDa MEP, these antibodies may be directly labeled or a labeled specific binding protein that specifically binds the polyclonal antibodies is used with polyclonal IgG (e.g., protein A conjugates) and capable of detecting the presence of antigen-antibody complex. For example, the F(ab')₂ fragments, F(ab) fragments or intact antibody molecules are capable of being immobilized on a support optionally supplied with the test kit.

Accordingly, the kit for diagnosing Lyme disease may comprise (a) anti-MEP antibodies or (b) labelled anti-MEP antibodies (c) anti-MEP antibodies and labeled anti-anti-MEP antibodies or labeled protein A or (d) anti-vesicle antibodies and anti-MEP antibodies, etc.

The F(ab')₂, F(ab) fragments, intact antibody molecules capable of binding *Borrelia burgdorferi* antigens, IgG preparations and reagents capable of reacting with polyclonal. IgG such as protein A conjugates may be in the form of a powder.

The present invention is also directed to a method of diagnosing Lyme disease in a mammal (e,g., human and domestic animals such as dogs, cats, horses, goats, sheep, cows, etc.) comprising the steps of taking a biological sample suspected of containing *Borrelia burgdorferi* antigens from a mammalian (e.g., human) host, capturing *Borrelia burgdorferi* antigens in said sample with F(ab')₂ fragments, F(ab) fragments or with intact antibody molecules raised against the extracellular membrane vesicles; and detecting the antigen with polyclonal antibodies raised against the 83 kDa MEP. The biological sample comprises, for instance, mammalian urine, blood, tears, cerebral spinal fluid, synovial fluid or the like, or organ. The organ or biopsied portion thereof is selected from the group consisting of macerated urinary bladder, spleen, liver, lung, brain tissue, heart, kidney and skin.

In addition, the present invention can be used to determine whether Ixodes or other ticks contain *Borrelia burgdorferi*. For example, the tick may be crushed in Dulbecco's phosphate-buffered saline pH 7.2 (dPBS) and used as the sample to be detected in the method of the present invention.

Moreover, the present invention is directed to an antigen comprising purified major extracellular protein isolated from *Borrelia burgdorferi*. Extracellular membrane vesicles were recovered from log phase cultures of *Borrelia burgdorferi* as described by Garon, et al. (1989). Structural features of *Borrelia burgdorferi*— the Lyme disease spirochete: silver staining for nucleic acids. Scanning Microscopy Supplement 3, pages 109–115. Cells were removed from the cultures by centrifugation at 20° C., for 20 min, at 10,000 x g. Cell removal was assured by further centrifugation for 15 min, at 20,000 x g, and by filtration through a 0.22 μm filter. Vesicles were recovered from this filtrate by centrifugation for 1 hr at 257,000 x g, at 20° C. Vesicle pellets were resuspended in dPBS, then layered onto a 10–70% step sucrose gradient and dPBS, and centrifugated for 2 hr at 259,000 x g at 4° C. Banded membranes were then removed, diluted 1:1 in dPBS, and collected by centrifugation for 15 rain at 435,000 x g at 4° C.

Such vesicles, when suspended at 1 mg per ml of dPBS, were used as immunogens in rabbits. Antibodies produced by rabbits immunized with vesicles were used to produce "anti-vesicle F(ab')₂ fragments." These vesicles were also used as a source from which a "MEP" antigen was purified.

Accordingly, the present invention is further directed to antigens of extracellular vesicles isolated by the steps of removing cells from *Borrelia burgdorferi* cultures by fractionation, for example, by centrifugation, filtering the cells and collecting a filtrate, recovering the vesicles from the filtrate, layering the vesicles on a sucrose gradient, and removing banded membranes from the sucrose gradient.

A major extracellular protein (MEP) antigen was purified electrophoretically from extracellular vesicle extracts, separated by sodium dodecylsulfate-polyacrylamide gel electrophoresis (Judd, R. C. (1988). Purification of outer membrane proteins of the Gram-negative bacterium *Neisseria gonorrhoea*. Anal Biochem. 173:307–316). The MEP is a protein with an apparent molecular mass of 83 kilodaltons (kDa), and it is shown in FIG. 1. It constitutes the major protein component of purified extracellular vesicles (as described above). The function of the MEP is unknown, however preliminary data suggested that the surface or s-layer of *Borrelia burgdorferi* was primarily made of the MEP.

Recent data has elucidated the composition and origin of the MEP. The 83 kDa MEP is composed of an extracellular multiprotein complex. To characterize the 83 kDa band resolved by electrophoresis, the N-terminus of the predominant peptide in the band was sequenced. Peptide sequence and amino acid composition comparisons showed identity with the heavy chain of immunoglobulin M (IgM). Reduction sensitivity experiments and the recognition of the band by antibodies specific for rabbit μ chain indicated that the multiprotein complex contained pentameric IgM. Immunoelectron microscopy showed that anti-μ chain antibodies and monoclonal antibodies to Osp A and Osp B bound to extracellular amorphous material surrounding cells. Furthermore, the Osps coprecipitated with either nonspecific polyclonal rabbit IgM antibodies or with murine monoclonal antihuman serum albumin IgM antibodies indicating that Osp A and Osp B are components of the 83 kDa MEP complex along with the predominant protein, nonspecific IgM. The origin of the IgM is rabbit serum which was used as a culture medium supplement (Dorward, D. W. et at. 1992, Infect. Immun. 60 (3): 838–844).

The purification of the MEP is set forth in Example 1, and it was used to immunize rabbits as described in Example 1. Polyclonal IgG produced by rabbits, in response to this protein was used as a detection reagent for the diagnostic test.

The present invention is further directed to an antibody raised against the antigens described above. For example, the invention is directed to anti-vesicle F(ab')₂ fragments which have a molecular mass of approximately 95 kDa. They have an antigen binding valence of 2, meaning that they can bind (iramobilize) two moles of antigen per mole of F(ab')₂. For example, a 1 μg/ml solution of F(ab')₂ fragments would contain approximately 10.5 picomoles, capable of binding up to 21 picomoles of antigen.

The F(ab')₂ fragments were made by digestion of anti-vesicle IgG with pepsin, followed by affinity chromatography, as described in Example 1. The IgG was accordingly purified from anti-vesicle serum by affinity chromatography with protein A-agarose, as described in Example 1. The F(ab')₂ fragments can bind and immobilize cell-surface and extracellular antigens produced by *Borrelia burgdorferi*, and they were used for such a purpose in this invention.

Moreover, the present invention is further directed to polyclonal antibodies raised against the 83 kDa MEP. These antibodies were produced by rabbits in response to immunization with purified MEP, and were purified by affinity chromatography as described in Example 1.

The anti-MEP IgG binds to the MEP, and to a protein at 31 kDa (Osp A), on immunoblots (FIG. 1), and it binds to cell-surface, and extracellular antigens produced by *Borrelia burgdorferi*. The anti-MEP IgG also binds to a protein at 34 kDa (Osp B) as shown in Dorward, Schwan & Garon, 1991 (J. Clin. Microbiol. 24:1162-1171). It does not bind to antigens produced by related spirochetes such as other species of Borrelia, and *Leptospira interrogans*. Anti-MEP IgG is used in this invention to detect antigens produced by *Borrelia burgdorferi*, that have been captured and immobilized by the anti-vesicle F(ab')$_2$ fragments.

EXAMPLE

MATERIALS AND METHODS

Bacteria. The bacteria used in this study are described in Table 1.

TABLE 1

| Bacteria used in Example 1. | | | |
|---|---|---|---|
| Organism | Strain | Source | Anti-MEP/GPA |
| B. burgdorferi | 19678 | P. leucopus, N.Y. | + |
| B. burgdorferi | 20004 | I. ricinus, France | + |
| B. burgdorferi | 26816 | Microtus, R.I. | + |
| B. burgdorferi | B31 | I. dammini, N.Y. | + |
| B. burgdorferi | G2 | Human CSF, Germany | + |
| B. burgdorferi | HB19 | Human blood, Conn. | + |
| B. burgdorferi | Sh-2-82 | I. dammini, N.Y. | + |
| B. anserina | | RML | − |
| B. coriaceae | CO53 | Ornithodorus coriaceus, Calif. | − |
| B. hermsii | HS1 | O. hermsi, Wash. | − |
| B. parkeri | | RML | − |
| B. turicatae | | RML | − |
| L. interrogans | | ATCC 23581 | − |

All bacteria from Table 1 were maintained in BSK II media described in (Barbour, A. G. 1984. Isolation and cultivation of Lyme disease spirochetes. Yale J. Biol. Med. 57:521-525). Whole cells (WC) and extracellular membrane vesicles were recovered by filtration and differential centrifugation as described in (Dorward, D. W., and R. C. Judd. 1988. The isolation and partial characterization of naturally-evolved outer membrane blebs of *Neisseria gonorrhoea*. p. 349-356. In Gonococci and Meningococci, J. T. Poolman, H. C. Zanen, T. J. Meyer, J. E. Heckels, P. R. H. Makela, H. Smith, and E. C. Beuvery (eds.), Kluwer Academic Publishers, Dordrecht, The Netherlands and Garon, C. F., D. W. Dorward, and M. D. Corwin. 1989 Structural features of *Borrelia burgdorferi*— the Lyme disease spirochete: silver staining for nucleic acids. Scanning Microscopy Supplement 3, pages 109-115).

Antibodies. Polyclonal rabbit sera were raised against membrane vesicles and the 83 kDa MEP, electrophoretically purified from vesicles (Dorward, D. W., and R. C. Judd. 1988. The isolation and partial characterization of naturally-evolved outer membrane blebs of *Neisseria gonorrhoea*. p. 349-356. In Gonococci and Meningococci, J. T. Poolman, H. C. Zanen, T. J. Meyer, J. E. Heckels, P. R. H. Makela, H. Smith, and E. C. Beuvery (eds.), Kluwer Academic Publishers, Dordrecht, The Netherlands and Judd, R. C. 1988. Purification of outer membrane proteins of the Gram-negative bacterium *Neisseria gonorrhoea*. Anal. Biochem. 173:307-316). Emulsions of antigen, and monophosphorylated lipid A and trehalose dimycolate (Ribi ImmunoChem, Inc., Hamilton, Mont.) were prepared according to manufacturer's instructions and used as primary immunogen. Immunized rabbits were periodically boosted with antigen suspended in dPBS. Sera were collected over a period of 10 weeks.

Immunoglobulin G (IgG) was purified from the sera by affinity chromatography with protein A-agarose (Sigma Chemical Co., St. Louis, Mo.). Eluted IgG was dialyzed overnight with water, and lyophilized for storage.

For some experiments, F(ab')$_2$ fragments were produced from IgG, directed against vesicles, by passage through pepsin-agarose (Sigma) as described in Lamoyi, E., and A. Nisonoff, 1983, Preparation of F(ab')$_2$ fragments from mouse IgG of various subclasses, J. Immunol. Methods 56:235-243. Cleaved IgG was subsequently passed through protein A-agarose and the void volume was retained. F(ab) fragments can be produced by passage through papain-agarose (Sigma) instead of pepsin-agarose as described above.

Experimental mouse infections. White-footed mice (*Peromyscus leucopus*) were experimentally infected with *B. burgdorferi* by intra-peritoneal injection with 0.1 ml suspensions of spirochetes in dPBS at an OD$_{600\,nm}$ of 0.4 (Schwan, T. G., W. Burgdorfer, and C. F. Garon. 1988. Changes in infectivity and plasmid profile of the Lyme disease spirochete, *Borrelia burgdorferi*, as a result of in vitro cultivation. Infect. Immun. 56:1831-1836 and Schwan, T. G., W. Burgdorfer, M. E. Schrumpf, and R. H. Karstens. 1988. The urinary bladder, a consistent source of *Borrelia burgdorferi* in experimentally infected white-footed mice (*Peromyscus leucopus*). J. Clin. Microbiol. 26:893-895). Urine, blood, and organs such as bladder, spleen, liver, kidney, heart and brain were collected from infected and uninfected animals. Infection was confirmed by culturing *B. burgdorferi* from triturated urinary bladders, as described in Schwan, T. G., W. Burgdorfer, and C. F. Garon, 1988, Changes in infectivity and plasmid profile of the Lyme disease spirochete, *Borrelia burgdorferi*, as a result of in vitro cultivation. Infect. Immun. 56:1831-1836 and Schwan, T. G., W. Burgdorfer, M. E. Schrumpf, and R. H. Karstens. 1988. The urinary bladder, a consistent source of *Borrelia burgdorferi* in experimentally infected white-footed mice (*Peromyscus leucopus*). J. Clin. Microbiol. 26:893-895.

Human, canine and tick materials. Clinical human urine and *Ixodes dammini* ticks, collected from Juneau County, Wisconsin, were graciously provided by Dr. Paul Duray. Human urine samples were also provided by laboratory volunteers. Acute human serum from Southampton, N.Y., was supplied by Dr. Alan MacDonald. Whenever possible, assays on human specimens were compared with serological data and/or patient histories. Urine and blood from a dog, naturally-infected in Bridgewater, N.J., were provided by Sara Stephens, D. V. M., Missoula, Mont.

Immunoblot analysis. Antigens, precipitated from urine with antiMEP antibodies, WC, and vesicles, were solubilized and subjected to sodium dodecylsulfate-polyacrylamide gel electrophoresis using the discontinuous buffer system of Laemmli (Laemmli, U. K. 1970. Cleavage of structural proteins during the assembly of the head of bacteriophage T4. Nature (London) 227:680-685), with the modifications described in Judd, R. C. 1982, $^{125}$I-peptide mapping of protein III isolated from four strains of *Neisseria gonorrhoea*, Infect. Immun. 37:622-631. Separated promins were electroblotted onto nitrocellulose, blocked with 0.05% Tween 20 in dPBS or 5% nonfat dry milk in dPBS, and probed with serum or IgG, as described in Batteiger, R., W. J. Newhall, and R. B. Jones, 1982, The use of Tween 20 as a blocking agent in the immunological detection of proteins transferred to nitrocellulose membranes, J. Immunol. Methods 55:297–307. Resulting immune complexes were labeled with protein A-horseradish peroxidase, and detected by chromogenic assay.

Electron microscopy. Copper grids were coated with Parlodion, then incubated for 10 rain, at room temperature, on a 6 μl droplet of anti-vesicle $F(ab')_2$ fragments dissolved at 1 μg per ml of dPBS. The grids were washed twice for 10 min with dPBS, then incubated for 10 min on a 6 μl droplet of antigen prepared as follows: urine, diluted 1:10 or as specified in dPBS; blood, diluted 1:10 in dPBS; and ticks or mouse organs such as bladder, spleen, liver, kidney, heart and brain, macerated in an equal volume of dPBS in glass tissue grinders. Following two, 10 min washings in dPBS, the grids were transferred onto 6 μl droplets of anti-MEP IgG and incubated at room temperature for 20 min. Two more dPBS washings were done, then antigen-antibody complexes were labeled for 20 min with 6 μl of protein A-colloidal gold conjugates, prepared by the methods of Robinson and co-workers (Robinson, E. N., Z. A. McGee, J. Kaplan, M. E. Hammond, J. K. Larson, T. M. Buchanan, G. K. Schoolnik. 1984. Ultrastructural localization of specific gonococcal macromolecules with antibody-gold sphere immunological probes. Infect. Immun. 46:361–366). The grids were washed twice for 5 min each in dPBS, twice for five min each in 0.25M ammonium acetate, then negatively stained with 0.5% ammonium molybdate, pH 6.5. The grids were dried in air, and observed at 75 kV with a model HU-11E-1 transmission electron microscope (Hitachi, Ltd., Tokyo, Japan).

RESULTS

To address whether membrane vesicles are released by *B. burgdorferi* in vivo, polyclonal rabbit antibodies were raised against vesicles and the 83 kDa MEP. After purification from collected sera, IgG from the rabbits was screened for reactivity with WC and vesicles by immunoblot analysis (FIG. 1). In FIG. 1, electroblotted whole cell (WC) and vesicle proteins were stained with buffalo black (B. Black), probed with polyclonal rabbit IgG generated against extracellular vesicles or the 83 kilodalton major extracellular protein (MEP), or probed with the anti-OspA monoclonal antibody, 5332 (Rocky Mountain Laboratories Collection). Anti-vesicle IgG recognized several WC and vesicle proteins, including OspA and OspB. The anti-MEP IgG recognized a 31 kilodalton protein, corresponding to OspA in WC and vesicle lanes. Accordingly, blotted proteins were either stained with buffalo black, or probed with anti-vesicle, polyclonal anti-MEP, or monoclonal anti-OspA antibodies, then labeled and detected as described above. Numerous WC and vesicle proteins were recognized by anti-vesicle IgG. Polyclonal IgG from rabbits immunized with the MEP, reacted primarily with a 31 kDa protein corresponding to OspA by electrophoretic migration. Only minimal labeling of the 83 kDa immunogen occurred. Reaction with monoclonal antibody 5332 confirmed the presence of OspA in WC and vesicles. With prolonged immunization of rabbits with the 83 kDa MEP, the sera showed reactivity with both the Osp A and Osp B proteins. (Dorward, Schwan, & Garon, 1991, J. Clin. Microbiol. 29:1162–1171). Sera taken from rabbits after a few immunization with MEP and sera taken from rabbits after prolonged immunization with MEP gave similar results in the immune capture assay for detection of *B. burgdorferi* antigens.

To determine whether these polyclonal sera could be used to concentrate and specifically detect intact WC and elaborated vesicles, Parlodion-coated electron microscope grids were absorbed with $F(ab')_2$ fragments made from anti-vesicle IgG. Such "activated" grids were incubated either in vitro cultures of *B. burgdorferi* or with media alone. Antigens adhering to the grids were detected with anti-MEP IgG and protein A-colloidal gold conjugates (FIG. 2). FIGS *2a–2c* describes the parlodion-coated grids were activated with anti-vesicle $F(ab')_2$ fragments, then incubated with cultured *B. burgdorferi* cells (*2a, b*) or with culture media (*2c*). The grids were then probed with anti-MEP IgG (*2a, c*) or pre-immune serum (*2b*), labeled with protein A-colloidal gold conjugates, and examined by electron microscopy. Gold particles adhered to cell and vesicle surfaces and to flocculent material surrounding cells. Only background levels of gold were observed on grids incubated with media, or probed with pre-immune serum. Bars, 200 nm. Both WC and vesicles adhered to activated grids. Heavy labeling was evident on the surfaces of cells and vesicles, and on flocculent material surrounding these structures. Sparse deposition of gold on the control grids lacking antigen, or incubated with pre-immune serum, was considered non-specific background.

To determine the specificity of the anti-MEP polyclonal IgG seven strains of *B. burgdorferi*, five other Borrelia species, and *Leptospira interrogans* (Table 1) were assayed. All seven *B. burgdorferi* isolates from the U.S. and Europe were specifically labeled, whereas the other spirochetes retained only background levels of gold.

Activated grids were then incubated with possible in vivo sources of *B. burgdorferi* antigens to assess the possibility of adapting this system to clinical samples. The samples tested included macerated Ixodes sp. ticks, specimens of urine, blood, or macerated tissues from mice, dogs, and humans (FIGS. 3, 3*a*–3*f*, 4*a*–4*h*).

FIG. 3 discloses the immune electron microscopic detection of *B. burgdorferi* antigens in mammalian urine and blood. Parlodion-coated grids were activated with anti-vesicle $F(ab')_2$ fragments, incubated with urine or blood samples, probed with anti-MEP IgG, and labeled with protein A-colloidal gold conjugates. Heavily-labeled flocculent antigens were aggregated on grids incubated with urine from infected mice, dogs, and humans (3*a, c, d*, respectively), and with blood from infected mice (3*b*). Labeled membrane vesicles were occasionally observed (3*a*, insert). No specific labeling was observed in urine and blood from uninfected mice (3*e, f*). Bars, 200 nm.

Capture and labeling of flocculent antigen was evident in urine and blood of five experimentally-infected mice (3*a, b*). Some fields contained labeled membranous structures resembling vesicles (FIG. 3*a*, insert). Similar flocculent material was evident in urine from a naturally-infected dog (3*c*) and a clinical human patient (3*d*). Labeled flocculent antigen was detected in mouse urine diluted up to $2\times10^{-6}$ in dPBS. No evidence of material, specifically labeled with gold, was detected in samples from uninfected mice or humans (3e, f). A total of 39 human urine samples were tested. These included two negative samples provided by laboratory personnel, and 37 clinical samples from patients suspected of having Lyme disease. A single clinical sample was negative, while 36 had aggregates of flocculent antigen.

The macerated tissues examined included ticks, urinary bladder, spleen, liver, heart, brain, and kidney (FIGS. 4a-g, respectively). FIG. 4 discloses the detection of *B. burgdorferi* antigens in macerated ixodid ticks and mouse tissues. Electron microscope grids were activated, incubated with macerated tissue, and precipitated antigens were labeled with anti-MEP IgG and protein A-colloidal gold conjugates. When examined, flocculent antigens were observed on grids incubated with infected *Ixodes dammini* ticks, and urinary bladder, spleen, liver, heart, and brain from infected *Peromyscus leucopus*(4a-f, respectively). Infected *P. leucopus* kidney had relatively dense labeling, but antigen aggregates were not observed on such grids (4g). Little gold was observed on control grids lacking antigen (4h). Bars, 200 nm. All but kidney specimens contained flocculent antigen. Although, kidney tissue was labeled more densely than control grids, antigen aggregates were not resolved. However, intact spirochetes were found on grids incubated with bladder tissue from four or five mice examined (4b, insert). Spirochetes were also observed in the blood and spleen of a single mouse at 12 days post-infection (data not shown). Only background levels of gold were observed in control grids lacking antigen (4h).

Figure 5:
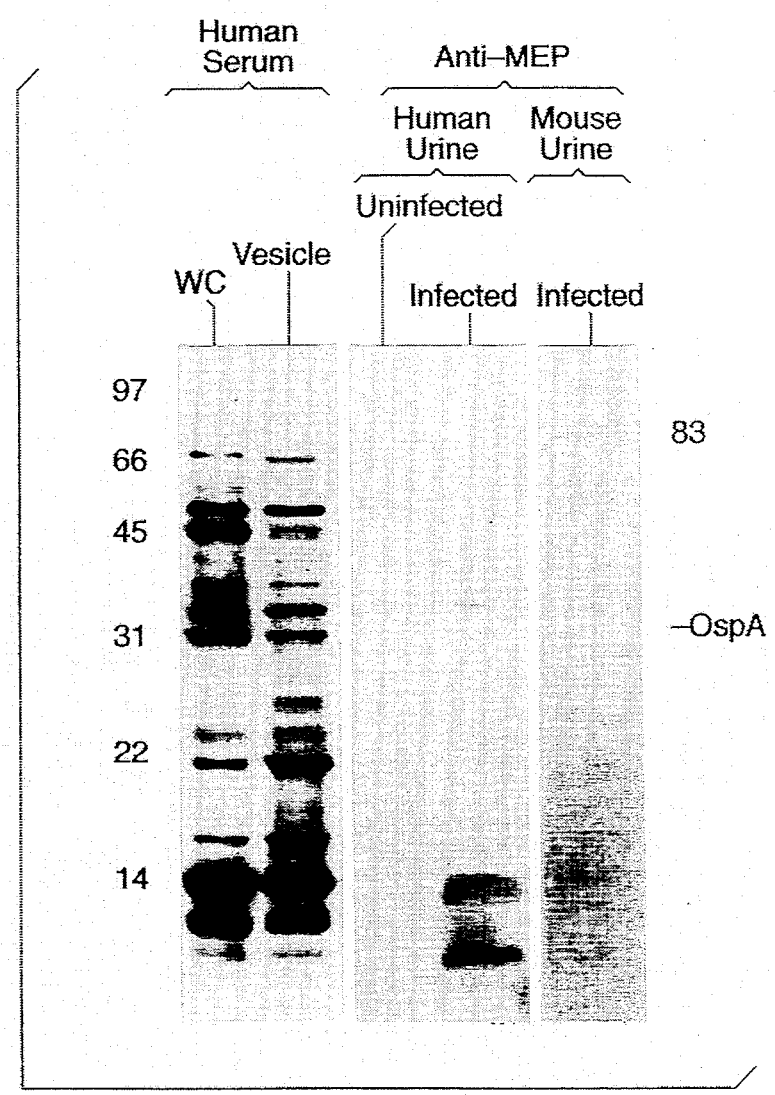
FIG. 5. Immunoblot analysis of *B. burgdorferi* antigens, precipitated from infected mouse and human urine.
Figure 6:
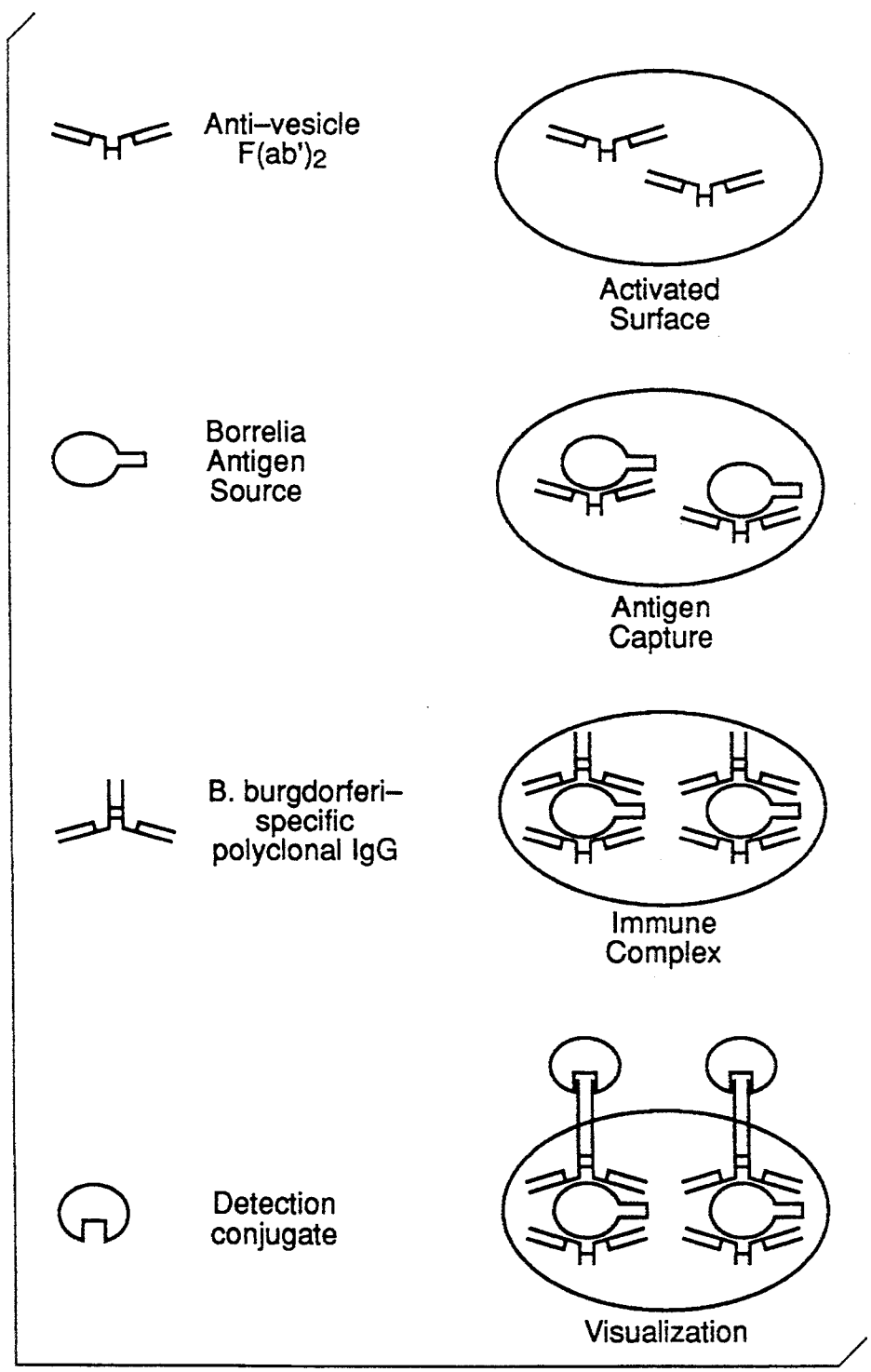
FIG. 6. Immune capture and detection of *B. burgdorferi* antigens.

To identify antigens detected in urine from humans and mice, the samples were incubated with anti-MEP IgG, and resulting precipitants were recovered and compared to WC and vesicle antigens by immunoblot analysis (FIG. 5). FIG. 5 discloses immunoblot analysis of *B. burgdorferi* antigens, precipitated from infected mouse and human urine. The banding patterns of whole cell (WC) and vesicle antigens, detected with acute human serum, was compared with immunoblots containing antigens, precipitated from human and mouse urine with anti-MEP IgG and detected by solid phase ELISA with anti-MEP IgG. At least five bands at 34, 31, 22, 14, and 11 kilodaltons were revealed in human urine precipitants, whereas a single band at 83 kilodaltons was detected in infected mouse preparations. When blotted WC and vesicle antigens were probed with acute human serum, numerous bands were resolved. No antigens were detected in urine from two uninfected humans (data not shown). However, the anti-MEP antibody recognized at least five bands ranging from 11-34 kDa in the urine precipitant from an infected human, and an 83 kDa band was detected in the mouse urine sample. These bands all corresponded by electrophoretic migration to WC and vesicle antigens observed with acute human serum.

EXAMPLE 2

IMMUNE CAPTURE OF BORRELIA BURGDORFERI ANTIGENS

As a primary source of reagents, *Borrelia burgdorferi* strain SH-2-82 is maintained, at low passage, in BSK II medium. Extracellular membrane vesicles are recovered by filtration and differential centrifugation of cultures, for use in antibody development.

For use in concentrating and detecting Lyme antigens, polyclonal rabbit sera are raised against membrane vesicles and a 83 kDa protein electrophoretically purified from the vesicles. Immunized rabbits are periodically boosted with antigen suspended in Dulbecco's phosphate-buffered saline pH 7.2 (dPBS). Sera raised against each immunogen are collected and pooled. Immunoglobin G (IgG) is purified from the pooled sera by affinity chromatography with protein A-agarose. Eluted IgG is either dialyzed overnight with water and lyophilized for storage, or used directly.

Anti-vesicle IgG is processed further as follows: F(ab')$_2$ fragments are produced from IgG directed against vesicles by passage through pepsin-agarose. Digested IgG is then passed through protein A-agarose and the void volume is retained. The anti-vesicle F(ab')$_2$ fragments are then absorbed to a solid surface, appropriate for subsequent incubation with biological sample. Such surfaces include, but are not limited to, Parlodion-coated electron microscopy grids, nitrocellulose filter membranes, glass cover slips, and microtiter wells. These steps provide an "activated" support for the capture and concentration of Borrelia antigens from a test sample. These steps also remove the Fc piece from the antivesicle IgG, that would interfere with the antigen detection procedures described below.

Fresh or refrigerated blood or urine is diluted from 1:10 to 1:100 in Dulbecco's phosphate-buffered saline at pH 7.2 (dPBS). Tissue biopsies or ticks are macerated with a tissue grinder in 1-10 ml of dPBS per gram of specimen. Test samples are then incubated for 10-30 min at room temperature in contact with the F(ab')$_2$-coated support. During this incubation, Borrelia antigens, if present, are removed from the sample and retained on the activated support. The support is then washed twice for 10 min in dPBS.

Anti-83 kDa IgG is reconstituted at 50 μg per ml of dPBS, placed in contact with supports containing test or control specimens, and incubated for 10-30 min at room temperature. Unbound IgG is removed by two 10 min washes in dPBS. The presence of antigen-antibody complexes on the supports is detected with protein A conjugates, that bind specifically to the Fc portion of the IgG. Commercially-available conjugates appropriate for various assay systems include: colloidal gold for electron microscopy and visual chromogenic assays, fluorescein isothiocyanate or rhodamine for fluorescent microscopy, latex beads for light microscopy, and horseradish peroxidase and alkaline phosphatase for enzyme-linked immunosorbent assays (ELISA) with visual or light microscopic screening.

EXAMPLE 3

METHOD OF PURIFYING EXTRACELLULAR MEMBRANE VESICLES.

Extracellular membrane vesicles are recovered from log phase cultures of *Borrelia burgdorferi* as described by Garon, et al. (1989) Structural features of *Borrelia burgdorferi*— the Lyme disease spirochete: silver staining for nucleic acids, Scanning Microscopy Supplement 3, pages 109-115. Cells are removed from the cultures by centrifugation at 20° C., for 20 min, at 10,000 x g. Cell removal is assured by further centrifugation for 15 min, at 20,000 x g, and by filtration through a 0.22 μm filter. Vesicles are recovered from this filtrate by centrifugation for 1 hr at 257,000 x g, at 20° C. Vesicle pellets are resuspended in dPBS, then layered onto a 10-70% step sucrose gradient in dPBS, and centrifugated for 2 hr at 259,000 x g at 4° C. Banded membranes are then removed, diluted 1:1 in dPBS, and collected by centrifugation for 15 min at 435,000 x g at 4° C.

Such vesicles, when suspended at 1 μg per ml of dPBS, are used as immunogens in rabbits. Antibodies produced by rabbits immunized with vesicles are used to produce "anti-vesicle F(ab')2 fragments." These vesicles are also used as a source from which a "MEP" antigen is purified.

EXAMPLE 4
METHOD OF PURIFYING MEP

Sodium dodecylsulfate extracts or purified extracellular vesicles are loaded into preparative 12.5 % polyacrylamide gels and electrophoresed for 2.5 hr at 7.5 watts, constant power. The gels are then stained with 0.25% Coomassie brilliant blue in water, and the MEP protein is identified by electrophoretic migration (the MEP protein band is the largest and darkest by far) and excised from the gel. The excised gel fragment is then loaded onto a 7.5 % preparative polyacrylamide gel and electrophoresed as described above. Proteins contained in the second gel are electroblotted onto nitrocellulose membranes and stained with 1% buffalo black in water. The segment of each membrane containing the MEP is excised and boiled in two changes of 200 µl of 10% SDS to elute the protein. The protein is then precipitated with acetone, and recovered by centrifugation for 30 min at 100,000 x g, and 4° C.

EXAMPLE 5
DETECTION OF *BORRELIA BURGDORFERI* ANTIGEN IN TEARS

Samples of tears from 37 individuals were collected on strips of sterile filter paper, and placed in *Borrelia burgdorferi* growth medium (BSKII). The samples were processed as described in Example 2 for the immune capture and detection of *B. burgdorferi* extracellular antigens. Of the samples tested, 36 were scored as positive for the presence of extracellular antigen aggregates and one sample was negative.

EXAMPLE 6
BACTERIA USED IN IMMUNE CAPTURE OF MICROORGANISMS

*Borrelia burgdorferi* strain Sh-2 was maintained in BSK II media as previously described (Barbour, A. G. 1984. Yale J. Biol. Med. 57:521–525). The infection studies described were performed using organisms from in vitro passage 7 (low passage) and >250 (high passage). *Escherichia coli* and *Staphylococcus aureus* strains 11775 and 12600 (American Type Culture Collection, Rockville, Md.) were grown at 37° C. in Luria broth.

EXAMPLE 7
INFECTION OF ANIMALS FOR IMMUNE CAPTURE OF MICROORGANISMS

Ixodes dammini ticks and white mice were infected with *B. burgdorferi* as previously described (Burgdorfer, W. et al. 1982. Science 216: 1317–1319; Schwan, T. G. et al. 1987. J. Infect. Dis. 156:852–853). Tick infections were verified by dark field microscopy prior to primary isolation experiments. After six weeks, the mice were sacrificed and the urinary bladders and spleens were recovered and triturated, as previously described (Schwan, T. G. et al. 1987. J. Infect. Dis. 156: 852–853). Midguts from experimentally infected ticks were also excised and prepared for culture, according to previously-published procedures (Burgdorfer, W. et. al. 1982. Science 216: 1317–1319; Burgdorfer, W. 1984. Yale J. Biol. Med. 57: 521–525). One half of each sample was inoculated into BSK II, and the remainder was utilized for capillary tube isolation procedures described below.

EXAMPLE 8
CAPILLARY TUBE PREPARATION FOR IMMUNE CAPTURE OF MICROORGANISMS

Figure 7:
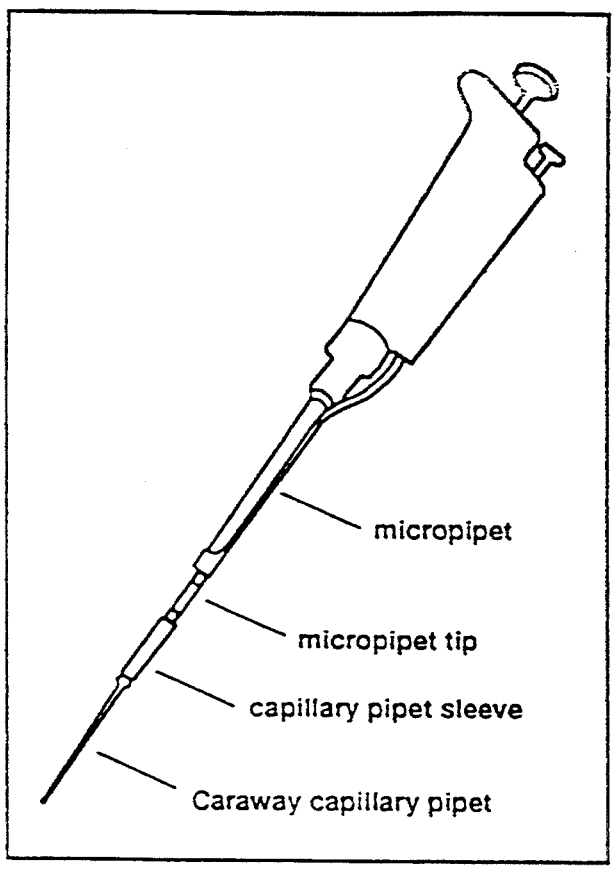
FIG. 7. Shows a micropipettor equipped with a 1–200 ul polypropylene tip, which has been clipped off to allow insertion of a capillary pipet sleeve.
Figure 8:
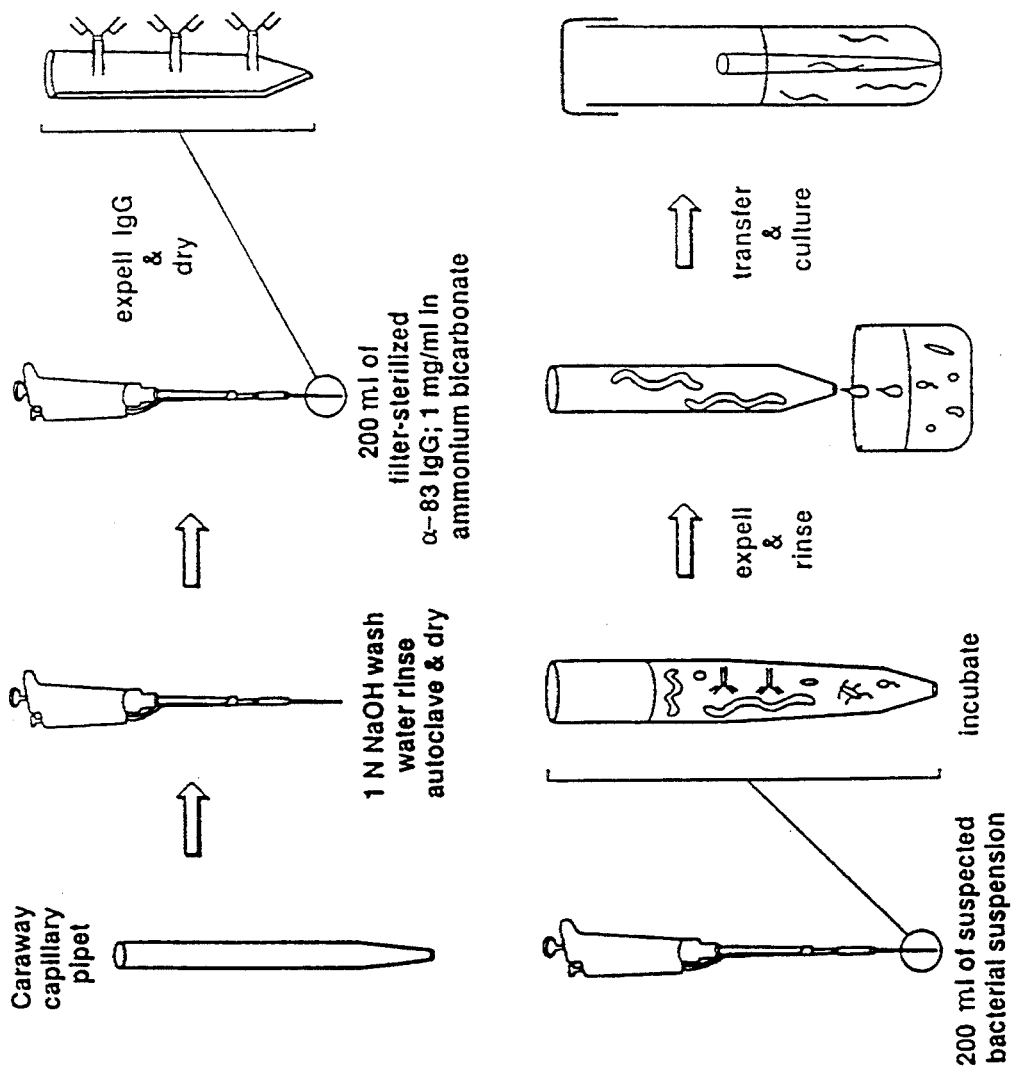
FIG. 8. A schematic diagram of the immune capture and cultivation procedure.

An apparatus capable of both manipulating Caraway capillary tubes (Fisher Scientific, Pittsburgh, Pa.), and repeatedly filling and evacuating the tubes was designed and constructed for this study (FIG. 7). The figure shows a micropipettor equipped with a 1–200 µl polypropylene tip, which has been clipped off to allow insertion of a capillary pipet sleeve (Baxter Healthcare Corporation, McGaw Park, Ill. FIG. 8 depicts a schematic diagram of the immune capture and cultivation procedures. Caraway capillary tubes were cleaned and etched by immersion in 1N NaOH, for one hour at room temperature. After thoroughly rinsing in distilled water, the tubes were sterilized by autoclaving and dried. Once dried, the tubes were "activated" with antibodies as follows. Purified IgG antibodies derived from rabbit serum generated against extracellular membrane vesicle concentrates or against a gel-purified, 83 kDa major extracellular protein band, were dissolved at 1 mg per ml of 0.1M ammonium bicarbonate and filter-sterilized through 0.2 µm membranes (Anotec Separations Ltd., Banbury Oxon, UK). A 200 µl volume of each antibody solution, or of 0.1M ammonium bicarbonate, was drawn aseptically into the capillary tubes and expelled. Each tube was then placed horizontally into a sterile container and the tubes were dried under vacuum at room temperature. Once dried, the tubes were either used immediately or stored at −20° C. For some experiments, ammonium bicarbonate was replaced by Dulbecco's phosphate-buffered saline pH 7.2. However, tubes coated with phosphate-buffered saline were used immediately because drying and storage left salt deposits in the tubes.

EXAMPLE 9
IMMUNE CAPTURE TECHNIQUE AND CULTIVATION PROCEDURE

Following tube preparation, antibody-activated or non-activated capillary tubes, treated with buffer only, were used for isolating and culturing *B. burgdorferi* from in vitro cultures and in vivo sources. For in vitro experiments, pure cultures of *B. burgdorferi*, or mixed cultures of *B. burgdorferi* and either or both *E. coli* and *S. aureus*, were titrated by ten-fold dilutions into sterile 12×100 mm culture tubes (Becton Dickinson Co., Oxnard, Calif.). The final volume in each culture tube was 2 ml. Following dilution, activated or non-activated capillary pipets were placed in the tubes and incubated at room temperature. After one hour, the tubes were removed and washed by drawing 200 µl of sterile 0.1M ammonium bicarbonate into the tube, and expelling the buffer. Five such washes were performed. The tubes were then placed into 12×100 mm culture tubes containing 3 ml of BSK II medium and incubated at 35° C. for up to three weeks, or until growth was evident in the tubes. The presence of spirochetes in such cultures was verified by dark field microscopy.

For capture and cultivation of spirochetes from in vivo sources, 100 µl of triturated mouse tissue, or tick midgut preparation was drawn into an activated capillary tube. The tube was then placed horizontally into a sterile beaker and incubated for 1 hr at room temperature. Following incubation the tubes were repeatedly washed in ammonium bicarbonate and placed in tubes containing culture medium as described above. An equal volume of triturate was also placed directly into culture tubes containing 3 ml of medium.

EXAMPLE 10

IMMUNE CAPTURE AND CULTIVATION OF B. BURGDORFERI FROM IN VITRO MIXED CULTURES

The previous examples showed that surfaces activated with F(ab$_2$') fragments or IgG antibodies, directed against *B. burgdorferi* extracellular membrane vesicle concentrates, could capture *B. burgdorferi* antigens and concurrently reduce adsorption of an excess of biological material from other sources to these activated surfaces. In order to determine whether such activated surfaces could be adapted to the capture and culture of *B. burgdorferi*, an apparatus was designated and constructed for manipulating capillary tubes, which could be activated and utilized for these purposes (FIGS. 7 and 8). FIG. 7 shows the apparatus, which can be adapted for use with a variety of micropipetting devices available commercially. This instrument facilitated repeated aseptic filling and expelling of precise volumes of the solutions and suspensions used in these experiments. FIG. 8 is a schematic representation of methods used in this study.

In order to determine whether antibody-activated capillary tubes could be used to capture and cultivate *B. burgdorferi* cells, capillary tubes, activated with either anti-vesicle or anti-83 kDa IgG antibodies, or non-activated capillary tubes, were incubated in culture tubes containing serial ten-fold dilutions of log-phase cultures, then rinsed and transferred the capillary tubes into fresh medium. The recovery of spirochetes from medium intentionally contaminated with *E. coli* was examined. In these experiments, cultures were supplemented with 50 µg of rifampin per ml of medium in order to mimic conditions used for primary isolations from ticks and mammals (Barbour, A. G. 1984. Yale J. Biol. Med. 57: 521–525). The results are shown in Table 2.

Table 2 shows the inverse log values of dilutions from which growth of either *B. burgdorferi* or *E. coli* occurred after transfer into fresh culture medium. Each value is the average of two dilution experiments. At least 10[7] spirochetes per ml of medium were present in the original culture. Without antibody activation, 2–3 logs fewer spirochetes were recovered in cultures incubated by capillary tube transfers. Transfers using capillary tubes coated with either antibody dissolved in phosphate-buffered saline resulted in 10–100% recovery of *B. burgdorferi*. Recovery of 1–10% of spirochetes was observed using antibodies dissolved in ammonium bicarbonate. When approximately equal numbers of *E. coli* cells were added to *B. burgdorferi* cultures and the mixtures were serially diluted, growth of *E. coli* was evident overnight. No attempt was made to quantify spirochetes in such mixtures. As with pure *B. burgdorferi* cultures, the numbers of *E. coli* recovered after transfer via non-activated capillary tubes were reduced by 2–3 logs. Approximately the same reduction in numbers of *E. coli* occurred using antibody-activated tubes. In several cases, using either antibody dissolved in either buffer, pure cultures of *B. burgdorferi* were recovered from the mixtures at dilutions greater than those resulting in growth of *E. coli*. Because of these results showing purification of *B. burgdorferi* in both buffer systems, and because of the preparative advantages cited above, ammonium bicarbonate system was used for all further experimentation.

TABLE 2

| | Inverse log of endpoint dilution resulting in growth of *Borrelia burgdorferi* or *Escherichia coli* | | | |
|---|---|---|---|---|
| | Phosphate-buffered saline | | Ammonium bicarbonate | |
| Sample | *B. burgdorferi* | *E. coli* | *B. burgdorferi* | *E. coli* |
| *B. burgdorferi* | | | | |
| Original culture | 7 | — | 7 | — |
| Tubes/buffer | 3.5 | — | 3 | — |
| Tubes/anti-vesicle | 7 | — | 5 | — |
| Tubes/anti-83 | 7 | — | 4.5 | — |
| *B. burgdorferi* and *E. coli* | | | | |
| Mixed culture | ND | 7 | ND | 7 |
| Tubes/buffer/no antibody | ND | 4.5 | ND | 5 |
| Tubes/anti-vesicle | 7[1] | 3.5 | 6[1] | 5 |
| Tubes/anti-83 | 7[1] | 4 | 5.5[2] | 4.5 |

ND = Not determined (contaminated).
[1]*B. burgdorferi* recovered from two of four mixed cultures.
[1]*B. burgdorferi* recovered from three of four mixed cultures.

The effect of deletion of rifampin from BSK II medium on the recovery of *B. burgdorferi* from mixed cultures was also examined (Table 3). In these experiments, *S. aureus* was added to mixtures of *E. coli* and *B. burgdorferi*. Preliminary experiments had shown that *S. aureus*, a common contaminant of skin biopsies, was inhibited by BSK II containing rifampin. Like Table 2, Table 3 lists the average inverse log value of endpoint dilutions containing viable bacteria from four dilution experiments. As described above, capillary tubes prepared without antibody reduced the transfer efficiency of *B. burgdorferi* by 2–3 logs, and the recovery of *B. burgdorferi* from diluted cultures using antibody-activated capillary tubes ranged from 10–100%. Adsorbed antibodies also reduced the numbers of *E. coli* and *S. aureus* present in capillary tube transfers from mixed cultures by more than 2 logs. Furthermore, pure cultures of *B. burgdorferi* were recovered from two of four and three of four bacterial mixtures, using capillary tubes activated with anti-vesicle and anti-83 kDa antibodies, respectively.

TABLE 3

| Inverse log of endpoint dilutions from mixed cultures, without antibiotics | | |
|---|---|---|
| Sample | *B. burgdorferi* | Mixed |
| *B. burgdorferi* | | |
| Original culture | 7.67 | — |
| Tubes/buffer | 4.75 | — |
| Tubes/anti-vesicle | 6.75 | — |
| Tubes/anti-83 | 7.5 | — |
| *B. burgdorferi*, *E. coli*, and *S. aureus* | | |
| Mixed culture | ND | 8.33 |
| Tubes/buffer | ND | 8.33 |
| Tubes/anti-vesicle | 7.5[1] | 6 |
| Tubes/anti-83 | 8[2] | 6 |

ND = Not determined (contaminated).
[1]*B. burgdorferi* recovered from two of four mixed cultures.
[2]*B. burgdorferi* recovered from three of four mixed cultures.

EXAMPLE 11

IMMUNE CAPTURE AND CULTIVATION OF B. BURGDORFERI FROM INFECTED TICKS AND MICE

For analysis of ticks, the midguts of three ticks infected with *B. burgdorferi* were removed, examined by dark field microscopy for spirochetes, and cultured both by direct inoculation of medium and by the antibody-activated capillary tube methods. After 24 hr, all three samples cultured directly were visibly contaminated with bacteria, whereas no contamination was evident in the capillary tube cultures. After nearly two weeks, two of the three capillary tube cultures showed fungal contamination. *B. burgdorferi* was recovered from the remaining culture. In a mammalian experiment, bladders and spleens from two mice infected with virulent spirochetes and two mice inoculated with high avirulent spirochetes were supplied as "blind" samples. These samples were also cultured with and without use of antibody-activated capillary tubes. Pure cultures of *B. burgdorferi* were recovered from both bladders and one spleen from animals infected with low passage organisms, whereas no isolates were obtained from direct inoculations into culture medium. Spirochetes were not cultured from animals inoculated with high passage spirochetes by either method.

EXAMPLE 12

IMMUNE CAPTURE AND CULTIVATION OF BACTEROIDES FRAGILIS

Monoclonal antibodies to the lipopolysaccharide (LPS) of *Bacteroides fragilis* or to a D-galactose oligomer of *B. fragilis* are produced as described by LinkoKettunen, L. et al. 1984, J. Clin. Microbiol. 20(3): 519–24 and Viljanen, M. K. et al 1988, J. Clin. Microbiol. 26(3); 448–452, both incorporated herein by reference. Capillary tubes are activated by coating the tubes with the anti-*B. fragilis* monoclonal antibodies. The coating procedure is as described in Example 8. A sample is taken from the perineal area of a patient suspected of having a bacteroides infection. One hundred microliters of sample are drawn into an activated capillary tube. The tube is placed horizontally into a sterile beaker and incubated for 1 hr. at room temperature. Following incubation, the tubes are repeatedly washed in ammonium bicarbonate and placed in tubes containing culture medium and grown under anaerobic conditions.

EXAMPLE 13

IMMUNE CAPTURE AND CULTIVATION OF RICKETTSIA AKARI

Monoclonal antibodies specific for Rickettsia akari are produced as described by McDade, J. E. et al. 1988, J. Clin. Microbiol. 26 (10): 2221–2223, incorporated herein by reference. Capillary tubes are activated by coating the tubes with the anti-*R. akari* monoclonal antibodies as described in Example 8. Samples are taken from tissues or fluids of a patient suspected of having a rickettsial infection. The sample is drawn into an activated capillary tube and incubated horizontally for 1 hr at room temperature. Following incubation, the tubes are repeatedly washed in ammonium bicarbonate and placed in tubes containing culture medium and grown under appropriate conditions. For Rickettsia or Coxiella, which are obligate intracellular parasites, the microorganisms are cultivated in cell cultures and/or host animals.

EXAMPLE 14

IMMUNE CAPTURE AND CULTIVATION OF *LEGIONELLA PNEUMOPHILA* FROM WATER SAMPLES

*Legionella pneumophila* is immune captured from environmental water samples from various sources using capillary tubes activated with monoclonal antibody specific for *L. pneumophila*. The antibody is produced as described by Makin, T. et al. 1989, Epidemiol. Infect. 103(1): 105–112, incorporated herein by reference. The organisms, once captured by the specific antibody, are placed in culture medium and grown under suitable culture conditions.

All publications cited hereinabove are herein incorporated by reference.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

EXAMPLE 15

IMMUNE CAPTURE AND CULTIVATION OF MYCOBACTERIUM TUBERCULOSUM FROM INFECTED HUMANS

One of the most significant current and future public health problems is the re-emergence of tuberculosis. A particular concern is the advent of multi-drug resistant strains of *Mycobacterium tuberculosum*, which have appeared in several urban areas. Being very fastidious and slow growing, *M. tuberculosum* is quite difficult to culture from infected humans, and thus is well suited for targeting by the immune capture and cultivation system. A present method for cultivating this bacterium is beneficial for clinical antibiotic susceptibility testing.

Capillary tubes are activated by coating the tubes with antibodies specific for *M. tuberculosum* as described in Example 8. A sputum sample is taken from a patient suspected of having a *M. tuberculosum* infection. The sample is drawn into an activated capillary tube and incubated for a time sufficient to allow the targeted Genus species of microorganisms, *M. tuberculosum*, to adhere to the activated tube, at the appropriate temperature. Following incubation, the tubes are repeatedly washed in ammonium bicarbonate or other appropriate buffer to remove non-targeted microorganisms. The tubes containing the adherent target microorganisms are placed in appropriate culture medium and grown under optimal conditions for growth of *M. tuberculosum*. Optionally for antibiotic susceptibility testing, the adherent target microorganisms are placed in culture medium containing an antibiotic.

What is claimed is:

1. A method of detecting *Borrelia burgdorferi* or *Borrelia burgdorferi* antigens in a sample, said method comprising:
   a. providing:
      i) a fluid or tissue sample;
      ii) purified polyclonal antibodies or mixtures of monoclonal antibodies, said antibodies raised against the extracellular membrane vesicles exported from *Borrelia burgdorferi*; and, iii) purified antibodies or antigen-binding fragments of said antibodies raised against the major extracellular protein exported from *Borrelia burdorferi* having a molecular weight of approximately 83 kDa;

b. contacting said sample with said antibodies of step a(ii) and said antibodies and step a(iii), under conditions in which ternary immune complexes will form among said antibodies of steps a(ii) and a(iii) and any antigens associated with *Borrelia burdorferi* that may be present in said sample; and c. detecting the presence of said ternary immune complexes as a means of detecting *Borrelia brugdorferi* or *Borrelia burgdorferi* antigens.

2. Purified antibodies or antigen-binding fragments of said antibodies raised against purified extracellular membrane vesicles exported from *Borrelia burgdorferi*.

* * * * *

UNITED STATES PATENT AND TRADEMARK OFFICE
CERTIFICATE OF CORRECTION

PATENT NO. : 5,403,718
DATED      : April 4, 1995
INVENTOR(S) : Dorward et al.

It is certified that error appears in the above-indentified patent and that said Letters Patent is hereby corrected as shown below:

In the Drawings:

In Fig. 1 in right margin, replace "OspaA" with --OspA--.

In claim 1, part a(iii), col. 31, li. 3, replace "*burdorferi*" with --*burgdorferi*--.

In claim 1, part b, on col. 32, li. 1, replace "*burdorferi*" with --*burgdorferi*--.

In claim 1, part C, on col. 32, li. 4-5, replace "*brugdorferi*" with --*burgdorferi*--.

Signed and Sealed this

Sixteenth Day of April, 1996

BRUCE LEHMAN

*Attest:*

*Attesting Officer*   Commissioner of Patents and Trademarks